(12) United States Patent
Tabata et al.

(10) Patent No.: US 8,623,619 B2
(45) Date of Patent: Jan. 7, 2014

(54) PROCESS FOR PRODUCING L-AMINO ACID

(75) Inventors: Kazuhiko Tabata, Ibaraki (JP); Akihiro Senoo, Ibaraki (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 184 days.

(21) Appl. No.: 13/148,564

(22) PCT Filed: Feb. 9, 2010

(86) PCT No.: PCT/JP2010/051886
§ 371 (c)(1),
(2), (4) Date: Aug. 9, 2011

(87) PCT Pub. No.: WO2010/090330
PCT Pub. Date: Aug. 12, 2010

(65) Prior Publication Data
US 2012/0015409 A1    Jan. 19, 2012

(30) Foreign Application Priority Data
Feb. 9, 2009    (JP) ................................ 2009-027881

(51) Int. Cl.
C12P 13/04    (2006.01)
C12P 13/22    (2006.01)
C12N 9/00     (2006.01)
C12N 1/20     (2006.01)
C12N 15/00    (2006.01)
C07H 21/04    (2006.01)

(52) U.S. Cl.
USPC ........ 435/108; 435/106; 435/183; 435/252.3; 435/320.1; 536/23.2

(58) Field of Classification Search
None
See application file for complete search history.

(56) References Cited

U.S. PATENT DOCUMENTS

| | | | |
|---|---|---|---|
| 5,972,663 A | 10/1999 | Winterhalter et al. | |
| 6,858,406 B1 | 2/2005 | Vrljic et al. | |
| 7,632,663 B1 | 12/2009 | Eggeling et al. | |
| 2006/0019355 A1 | 1/2006 | Ueda et al. | |

FOREIGN PATENT DOCUMENTS

| | | | |
|---|---|---|---|
| EP | 1 253 195 A1 | 10/2002 | |
| JP | 11-056381 A | 3/1999 | |
| JP | 2002-537771 A | 11/2002 | |
| JP | 2005-237379 A | 9/2005 | |
| WO | WO 97/23597 A2 | 7/1997 | |
| WO | WO 01/53459 A1 | 7/2001 | |
| WO | WO 2008/044714 A1 | 4/2008 | |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession P27844, Aug. 1, 1992.*
Accession P31125, Jul. 1, 1993.*
Accession P31442, Jul. 1, 1993.*
Accession QOTHG4, Sep. 5, 2006.*
Daley et al., Science, 308: 1321-1323 (2005).
Dassler et al., Molecular Microbiology, 36(5): 1101-1112 (2000).
Livshits et al., Research in Microbiology, 154: 123-135 (2003).
Long et al., Antimicrobial Agents and Chemotherapy, 52(9): 3052-3060 (2008).
Nishino et al., Journal of Bacteriology, 183(20): 5803-5812 (2001).
Omote et al., Trends in Pharmacological Sciences, 27(11): 587-593 (2006).
Rouquette-Loughlin et al., Journal of Bacteriology, 185(3): 1101-1106 (2003).
Vrljic et al., Molecular Microbiology, 22(5): 815-826 (1996).
Yang et al., Journal of Antimicrobial Chemotherapy, 51: 545-556 (2003).
Japanese Patent Office, International Search Report in International Patent Application No. PCT/JP2010/051886 (May 11, 2010), English translation.
The International Bureau of WIPO, International Preliminary Report on Patentability in International Patent Application No. PCT/JP2010/051886 (Sep. 13, 2011), English translation.
Iguchi et al., Journal of Bacteriology, 191(1): 347-354 (2009).
Yamada et al., Applied and Environmental Microbiology, 72(7): 4735-4742 (2006).
Zakataeva et al., Microbiology, 75(4): 438-448 (2006).
European Patent Office, Supplementary European Search Report in European Patent Application No. EP 10 73 8658 (Jul. 17, 2012).

* cited by examiner

Primary Examiner — Christian Fronda
(74) Attorney, Agent, or Firm — Leydigs, Voit & Mayer, Ltd.

(57) ABSTRACT

The present invention provides a method of improving efficiency of a fermentative production of an L-amino acid. To be specific, the present invention provides a process for producing a L-amino acid, comprising culturing a microorganism wherein the activity of the protein described in any one of (1) to (3) below is higher than that of the parent strain in a medium to produce the L-amino acid and accumulate the L-amino acid in the medium, and then collecting the L-amino acid from the medium:

(1) a protein comprising the amino acid sequence shown by any one of SEQ ID NOS:2, 4, 6 and 8
(2) a protein consisting of the amino acid sequence resulting from deletion, substitution or addition of one or more amino acids in the amino acid sequence shown in any one of SEQ ID NOS:2, 4, 6 and 8, and having L-amino acid transport activity
(3) a protein consisting of the amino acid sequence having 80% or more homology to the amino acid sequence shown in any one of SEQ ID NOS:2, 4, 6 and 8, and having L-amino acid transport activity.

14 Claims, No Drawings

PROCESS FOR PRODUCING L-AMINO ACID

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 44,486 bytes ASCII (Text) file named "708793SequenceListing.txt," created Aug. 9, 2011.

TECHNICAL FIELD

The present invention relates to a process for producing an L-amino acid using a microorganism having the capability of producing the L-amino acid, and having the L-amino acid transport activity higher than that of the parent strain. More specifically, the present invention relates to a process for producing the L-amino acid wherein the L-amino acid productivity is increased by constructing a microorganism whose activity of transporting the L-amino acid from inside of the cell to outside of the cell is higher than that of the parent strain, allowing the microorganism to produce the L-amino acid, and efficiently exporting the produced L-amino acid from inside of the cell of the microorganism to outside of the cell.

BACKGROUND ART

Production of an amino acid by utilizing a microorganism is known as amino acid fermentation, and is traditionally widely conducted in the field of applied microbiology. In amino acid fermentation, in the final step thereof, amino acid transport activity, that is, how to facilitate the efflux of the resulting amino acid to the outside of the cell of the bacterium is an important process that influences amino acid productivity; various attempts have been made to date to increase the efficiency of efflux to the outside of the cell.

Usually, active transport using bioenergy is necessary to transport an amino acid in the cell of a microorganism to outside of the cell. Proteins that export intracellular amino acids to outside of the cell (efflux proteins) have been identified; it is known that amino acid productivity can be also conferred or enhanced by enhancing the expression of the proteins. For example, a process for producing L-lysine using a strain of a microorganism of the genus *Corynebacterium* wherein the expression of the L-lysine, L-arginine efflux gene (lysE) (see non-patent document 1) is enhanced (see patent document 1); a process for producing L-cysteine, L-cystine, N-acetylserine or thiazoline derivative using a strain of a microorganism of the genus *Escherichia* wherein the expression of the efflux gene (rhtA) of L-threonine, L-homoserine (see patent document 2), and L-cysteine, L-cystine, N-acetylserine or thiazoline derivative efflux gene (ydeD/eamA) (see non-patent document 3) are enhanced (patent document 2); a process for producing L-amino acids, including L-lysine, using a strain of a microorganism of the genus *Escherichia* wherein the expression of the L-lysine efflux gene (ybjE) involved in L-lysine resistance is enhanced (patent document 3) and the like are known.

However, no report is available on an efflux protein for L-serine and L-glutamine, and a process for producing the amino acids wherein the activity of the protein is enhanced.

By the way, the *Escherichia coli* norM gene is known to be an efflux pump gene related to quinolone resistance (non-patent document 4). The emrD gene is reported as an SDS transport gene (non-patent document 5). While rarD is predicted to be a drug transport gene, none of them is known to have an amino acid efflux activity (non-patent document 6). Meanwhile, the eamA(ydeD) gene is reported as a gene having efflux activity for L-cysteine, L-cystine, N-acetylserine or thiazoline derivative (non-patent document 3).

PRIOR ART DOCUMENTS

[Patent Documents]
   [patent document 1] WO97/23597
   [patent document 2] JP-A-11-56381
   [patent document 3] JP-A-2005-237379
[Non-Patent Documents]
   [non-patent document 1] Mol. Microbiol., 22, 815-826 (1996)
   [non-patent document 2] Res. Microbiol., 154, 123-135 (2003)
   [non-patent document 3] Mol. Microbiol., 36, 1101-1112 (2000)
   [non-patent document 4] J. Antimicrob. Chemother., 51, 545-56 (2003)
   [non-patent document 5] J. Bacteriol., 183, 5803-5812 (2001)
   [non-patent document 6] Science, 308, 1321-1323 (2005)

SUMMARY OF THE INVENTION

Problems to be Solved by the Invention

A problem to be solved by the present invention is to provide an efficient process for producing an L-amino acid by allowing a microorganism whose L-amino acid transport activity is higher than that of the parent strain to produce the L-amino acid. More specifically, the problem is to provide a novel manufacturing process of high productivity for the five neutral amino acids, including L-serine and L-glutamine, for which no manufacturing process based on enhanced L-amino acid transport activity has been available to date, by enhancing the efflux protein.

Means of Solving the Problems

Accordingly, the present invention relates to [1] to [4] below.
[1] A process for producing an L-amino acid which comprises; culturing a microorganism having L-amino acid transport activity wherein the activity of the protein described in any one of (1) to (3) below is higher than that of the parent strain in a medium, producing and accumulating the L-amino acid in the medium, and, collecting the L-amino acid from the medium:
  (1) a protein comprising the amino acid sequence shown in any one of SEQ ID NOS:2, 4, 6 and 8
  (2) a protein consisting of the amino acid sequence resulting from deletion, substitution or addition of one or more amino acids in the amino acid sequence shown in any one of SEQ ID NOS:2, 4, 6 and 8, and having L-amino acid transport activity
  (3) a protein consisting of the amino acid sequence having 80% or more homology to the amino acid sequence shown in any one of SEQ ID NOS:2, 4, 6 and 8, and having L-amino acid transport activity.
[2] The process for producing the L-amino acid according to [1], wherein the microorganism is transformed with the DNA described in any one of (1) to (3) below, or the microorganism is enhanced the expression of the gene by modifying the expression regulatory sequence of the DNA:

(1) a DNA that encodes for the protein described in any one of (1) to (3) in [1]
(2) a DNA having the nucleotide sequence shown in any one of SEQ ID NOS:1, 3, 5 and 7
(3) a DNA that hybridizes under stringent conditions with the DNA consisting of the nucleotide sequence complementary to the nucleotide sequence shown in any one of SEQ ID NOS:1, 3, 5 and 7, and encodes for the protein having L-amino acid transport activity.
[3] The process for producing the L-amino acid according to [1] or [2], wherein the microorganism belongs to the genus *Escherichia*, the genus *Corynebacterium*, the genus *Bacillus*, the genus *Serratia*, the genus *Pseudomonas* or the genus *Streptomyces*.
[4] The process for producing the L-amino acid according to any one of [1] to [3], wherein the L-amino acid is selected from the group consisting of L-serine, L-glutamine, L-cysteine, L-phenylalanine and L-threonine.

Effect of the Invention

The manufacturing process of the present invention is a manufacturing process that is highly productive in producing an L-amino acid, particularly L-serine, L-glutamine, L-cysteine, L-phenylalanine or L-threonine.

The manufacturing process of the present invention is a method of efficiently producing L-serine and L-glutamine using a microorganism by enhancing the activity of a protein having the activity of transporting an L-amino acid in the cell body of the microorganism to outside of the cell body. Also provided is a novel manufacturing process for L-cysteine, L-threonine and L-phenylalanine comprising enhancing the L-amino acid transport activity in the same way.

The inventor of this invention found that the publicly known transport gene norM, emrD or rarD of *Escherichia coli* has the function of transporting an amino acid to outside of the cell, and also found that these transport genes can be advantageously utilized for producing L-serine or L-glutamine, or L-cysteine, L-threonine, or L-phenylalanine.

The present inventor also newly found that eamA, which had been known to have L-amino acid transport activity, is also responsible for L-serine transport, and devised a process for producing L-serine by utilizing this.

According to the method of the present invention, enhancing the activity of the aforementioned amino acid transport genes makes it possible to remarkably improve the production of L-amino acids by selective active transport of the produced L-amino acid to outside of the cell. Additionally, the microorganism used to produce an L-amino acid does not depend on the type of outer membrane (presence or absence of cell wall, capsule, mucus layer and the like), whether it is Gram-positive or Gram-negative. Hence, the manufacturing process of the present invention is a manufacturing process of high versatility that can be used both for Gram-positive bacteria such as genus *Corynebacterium*, genus *Bacillus*, and genus *Streptomyces*, and for Gram-negative bacteria such as genus *Escherichia*, genus *Serratia*, and genus *Pseudomonas*.

The manufacturing process of the present invention dramatically improves the production efficiency for L-serine and L-glutamine compared with conventional processes. L-serine, in particular, is an amino acid that plays an important role in living organisms despite its identity as a non-essential amino acid, and is of high utility as a raw material for amino acid mixtures in the field of pharmaceuticals and the field of cosmetics. L-glutamine is an amino acid that acts to keep normal the functions of the stomach, intestines, muscles and the like in the body, and serves as a raw material for anti-alcoholism compositions and the like. If a highly productive manufacturing process for these L-amino acids is established to enable their industrial mass-production, its industrial applicability would be very high.

For L-cysteine, L-threonine and L-phenylalanine as well, the manufacturing process of the present invention has enabled more economic production. L-cysteine is an amino acid that is highly valuable in the cosmetic industry as a raw material for cosmetics because of its whitening effect. L-threonine and L-phenylalanine are both essential amino acids; L-threonine, as an ingredient of amino acid infusions and health foods, and L-phenylalanine, as a raw material for the low-calorie sweetener Aspartame (methyl ester of aspartylphenylalanine, 200 times as sweet as sugar), are useful amino acids whose productivity is expected to be improved by the manufacturing process of the present invention.

MODES FOR EMBODYING THE INVENTION

1. Microorganisms Used in the Manufacturing Process of the Present Invention

Microorganisms whose L-amino acid transport activity is higher than that of the parent strain Microorganisms whose activity of a protein having L-amino acid transport activity is higher than that of the parent strain are (a) microorganisms obtained by modifying a DNA that encodes for a protein having L-amino acid transport activity on the chromosomal DNA of the parent strain, wherein the microorganisms are i) a microorganism whose specific activity of the protein has improved compared with the parent strain, and ii) a microorganism whose production amount of a protein having L-amino acid transport activity has improved compared with the parent strain, and (b) microorganisms obtained by transforming the parent strain with a DNA that encodes for a protein having L-amino acid transport activity. As a parent strain mentioned herein, whether a wild type strain or a mutant strain can be used, and is the original strain which is the subject of modification or transformation. A wild type strain refers to the strain having the phenotype that is most frequently observed in a wild population. The parent strain includes, when the microorganism is *Escherichia coli*, for example, the wild type strains *E. coli* K-12 strain, B strain, B/r strain, and W strain, or strains that are mutants thereof; the mutant strains include *E. coli* XL1-Blue, *E. coli* XL2-Blue, *E. coli* DH1, *E. coli* MC1000, *E. coli* ATCC12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415, *E. coli* ATCC9637 and the like.

Proteins having L-amino acid transport activity include the proteins described in any one of (1) to (3) below:
(1) proteins comprising the amino acid sequence shown in any one of SEQ ID NOS:2, 4, 6 and 8;
(2) proteins consisting of the amino acid sequence resulting from deletion, substitution or addition of one or more amino acids in the amino acid sequence shown in any one of SEQ ID NOS:2, 4, 6 and 8, and having L-amino acid transport activity; and
(3) proteins consisting of the amino acid sequence having 80% or more homology to the amino acid sequence shown in any one of SEQ ID NOS:2, 4, 6 and 8, and having L-amino acid transport activity.

Here, the DNA sequences of SEQ ID NOS:1, 3, 5 and 7 encode for the aforementioned norM gene, emrD gene, rarD gene and eamA gene, respectively, in *Escherichia coli*; the amino acid sequences shown in the SEQ ID NOS:2, 4, 6 and 8 represent norM protein, emrD protein, rarD protein and eamA protein, respectively, encoded by the aforementioned genes.

A protein consisting of the amino acid sequence resulting from deletion, substitution or addition of one or more amino acid residues, and having L-amino acid transport activity in the above can be acquired by introducing a site-directed mutation into, for example, a DNA that encodes for the protein consisting of the amino acid sequence shown in any one of SEQ ID NOS:2, 4, 6 and 8, using one of the site-directed mutagenesis methods described in Molecular Cloning, A Laboratory Manual, Third Edition, Cold Spring Harbor Laboratory Press (1989) (hereinafter, abbreviated as Molecular Cloning, Third Edition), Current Protocols in Molecular Biology, John Wiley & Sons (1987-1997) (hereinafter, abbreviated as Current Protocols in Molecular Biology), Nucleic Acids Research, 10, 6487 (1982), Proc. Natl. Acad. Sci. USA, 79, 6409(1982), Gene, 34, 315 (1985), Nucleic Acids Research, 13, 4431 (1985), Proc. Natl. Acad. Sci. USA, 82, 488 (1985) and the like.

The number of amino acid residues deleted, substituted or added is not particularly limited; it is a number that can be deleted, substituted or added by an obvious method such as the above-described site-directed mutation methods, and is one to several tens, preferably 1 to 20, more preferably 1 to 10, still more preferably 1 to 5.

Deletion, substitution or addition of one or more amino acids in the amino acid sequence shown in SEQ ID NO:2, 4, 6 or 8 may be such that one or a plurality of amino acid residues are deleted, substituted or added at an optionally chosen position in the same sequence.

Positions where an amino acid residue can be deleted or added include, for example, 10 amino acid residues on the N-terminal side and C-terminal side of the amino acid sequence shown in any one of SEQ ID NOS:2, 4, 6 and 8.

A deletion, substitution or addition may occur concurrently; it does not matter whether the amino acid substituted or added is of the natural type or the non-natural type. Natural type amino acids include L-alanine, L-asparagine, L-aspartic acid, L-arginine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Examples of mutually replaceable amino acids are shown below. The amino acids included in the same group are mutually replaceable.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine Proteins having L-amino acid transport activity include a protein consisting of the amino acid sequence having 80% or more, preferably 90% or more, more preferably 95% or more, still more preferably 97% or more, particularly preferably 98% or more, most preferably 99% or more homology, to the amino acid sequence shown in any one of SEQ ID NOS:2, 4, 6 and 8, and having L-amino acid transport activity.

Amino acid sequence and nucleotide sequence homologies can be determined using the algorithm BLAST of Karlin and Altschul [Pro. Natl. Acad. Sci. USA, 90, 5873 (1993)] or FASTA [Methods Enzymol., 183, 63 (1990)]. Based on this algorithm BLAST, programs called BLASTN and BLASTX have been developed [J. Mol. Biol., 215, 403 (1990)]. When nucleotide sequences are analyzed with BLASTN on the basis of BLAST, parameters are set to, for example, score=100 and wordlength=12. When amino acid sequences are analyzed with BLASTX on the basis of BLAST, parameters are set to, for example, score=50 and wordlength=3. When the BLAST and Gapped BLAST programs are used, the default parameters of the respective programs are used. The specific ways of these analytical methods are well known.

Whether the protein consisting of the amino acid sequence resulting from deletion, substitution or addition of one or more amino acid residues in the amino acid sequence shown in any one of SEQ ID NOS:2, 4, 6 and 8, and having L-amino acid transport activity can be confirmed by, for example, a method wherein a transformant that expresses the protein whose activity is to be confirmed is prepared using a DNA recombination technique, and labeled L-amino acid and inside-out membrane vesicles that can be prepared from the transformant [J. Biol. Chem., 277, 49841 (2002)] are used [J. Biol. Chem., 280, 32254 (2005)].

Whether the protein consisting of an amino acid sequence resulting from deletion, substitution or addition of one or more amino acid residues in the amino acid sequence shown in SEQ ID NO:2, 4, 6 or 8, and having L-amino acid transport activity can also be confirmed by, for example, transforming the parent strain with a DNA that encodes for the protein whose activity is to be confirmed to prepare a transformant wherein the protein activity is higher than that of the parent strain, and comparing the amounts of L-amino acid produced and accumulated in the culture broths of the parent strain or the transformant.

The microorganisms above (a)-i) obtained by modifying a DNA that encodes for the protein having L-amino acid transport activity on the chromosomal DNA of the parent strain, wherein the specific activity of the protein has been improved compared with the parent strain, include a microorganism having a mutated protein whose L-amino acid transport activity has improved compared with the parent strain because it has a protein having the amino acid sequence resulting from substitution of 1 or more amino acids, preferably 1 to 10 amino acids, more preferably 1 to 5 amino acids, still more preferably 1 to 3 amino acids, in the amino acid sequence of the protein possessed by the parent strain.

The microorganisms above (a)-ii) obtained by modifying a DNA that encodes for the protein having L-amino acid transport activity on the chromosomal DNA of the parent strain, wherein the amount produced of the protein having L-amino acid transport activity has been improved compared with the parent strain, include a microorganism wherein the amount of the protein produced has been improved compared with the amount of the protein having L-amino acid transport activity produced by the parent strain because it has a promoter region wherein 1 base or more, preferably 1 to 10 bases, more preferably 1 to 5 bases, still more preferably 1 to 3 bases, are substituted in the nucleotide sequence of the transcription regulatory region or promoter region of the gene that encodes for the protein, present on the chromosomal DNA of the parent strain.

The microorganisms above (b) obtained by transforming a parent strain with the DNA that encodes for the protein having L-amino acid transport activity include microorganisms obtained by transforming the parent strain using:

[4] DNA that encodes for the protein described in any one of [1] to [3] above;

[5] DNA having the nucleotide sequence shown in any one of SEQ ID NO:1, 3, 5 and 7; or

[6] a DNA that hybridizes with the DNA consisting of the nucleotide sequence complementary to the nucleotide sequence shown in any one of SEQ ID NOS:1, 3, 5 and 7 under stringent conditions, and encodes for the protein having L-amino acid transport activity.

Such microorganisms include i) a microorganism having an extraneous DNA that encodes for the protein having L-amino acid transport activity on the chromosomal DNA, and ii) a microorganism having the same outside of the chromosome. Specifically, the microorganism i) is a microorganism having on the chromosome one or two or more newly introduced DNAs when the parent strain does not carry the DNA that encodes for the protein having L-amino acid transport activity, or a microorganism having on the chromosomal DNA two or more DNAs that encode for the protein having L-amino transport activity, including newly introduced DNA, when the parent strain originally carries the DNA that encodes for the protein having L-amino acid transport activity. The microorganism ii) is a microorganism having the DNA that encodes for the protein having L-amino acid transport activity on a plasmid DNA.

Herein, "L-amino acid transport activity" refers to the activity of effluxing an L-amino acid from inside of a cell to outside of the cell.

To "hybridize" as mentioned above means that a DNA hybridizes with another DNA having a particular nucleotide sequence or a portion of the DNA. Therefore, the DNA having a particular nucleotide sequence or a portion thereof can be used as a probe for Northern or Southern blot analysis, and can be also used as an oligonucleotide primer for PCR analysis. DNAs used as probes include DNAs of at least 100 bases or more, preferably 200 bases or more, more preferably 500 bases or more; DNAs used as primers include DNAs of at least 10 bases or more, preferably 15 bases or more.

Methods of DNA hybridization experiments are well known; for example, those skilled in the art are able to determine hybridization conditions according to the description of this application. The hybridization can be performed under conditions described in Molecular Cloning, 2nd edition and 3rd edition (2001), Methods for General and Molecular Bacteriolgy, ASM Press (1994), Immunology methods manual, Academic press (Molecular), and many other standard textbooks.

The above-described "stringent conditions" are preferably the conditions of incubating a DNA-immobilizing filter and a probe DNA in a solution containing 50% formamide, 5×SSC (750 mmol/l sodium chloride, 75 mmol/l sodium citrate), 50 mmol/l sodium phosphate (pH 7.6), 5×Denhardt's solution, 10% dextran sulfate, and 20 µg/l denatured salmon sperm DNA, at 42° C. overnight, followed by washing the filter in, for example, a 0.2×SSC solution at about 65° C., but lower stringent conditions can be used. The stringent conditions can be changed by adjusting the formamide concentration (as the formamide concentration is lowered, the stringency decreases), and changing the salt concentration and temperature conditions. Low stringent conditions include, for example, the conditions of incubation in a solution containing 6×SSCE (20×SSCE comprises 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, at 37° C. overnight, followed by washing using a 1×SSC, 0.1% SDS solution at 50° C. Still lower stringent conditions include the conditions of performing hybridization under the above-described low stringent conditions using a solution at a high salt concentration (for example, 5×SSC), followed by washing.

The above-described various conditions can also be set by adding or changing a blocking reagent used to suppress the background of the hybridization experiment. The addition of the blocking reagent may be accompanied by a change in the hybridization conditions to adapt the conditions.

DNAs that can be hybridized under the above-described stringent conditions include, for example, a DNA having at least 90% or more, preferably 95% or more, more preferably 97% or more, still more preferably 98% or more, particularly preferably 99% or more homology, to the DNA consisting of the nucleotide sequence shown in any one of SEQ ID NOS:1, 3, 5 and 7, as calculated on the basis of the above-described parameters and the like using the above-described BLAST, FASTA and the like.

2. Preparation of Microorganisms Used in the Present Invention (1) Preparation of Microorganism Wherein the Activity of the Protein Having L-Amino Acid Transport Activity is Higher than That of the Parent Strain Among the microorganisms wherein the activity of the protein having L-amino acid transport activity is higher than that of the parent strain, a microorganism wherein the specific activity is higher than that of the protein having L-amino acid transport activity of the parent strain can be acquired by introducing a mutation into a DNA that encodes for the protein having L-amino acid transport activity by subjecting the DNA to a mutation treatment using a mutagen in vitro, error-prone PCR or the like, then replacing the mutated DNA with the DNA before introduction of the mutation, that encodes for the protein having L-amino acid transport activity, present on the chromosomal DNA of the parent strain, using a publicly known method [Proc. Natl. Acad. Sci. USA., 97, 6640 (2000)] to prepare a modified strain that expresses the mutated DNA, and comparing the L-amino acid transport activities of the parent strain and the modified strain by the above-described method.

Among the microorganisms wherein the activity of the protein having L-amino acid transport activity is higher than that of the parent strain, a microorganism wherein the amount of the protein produced has been improved compared with the amount produced of the parent strain can be identified by a method wherein a mutation is introduced into a DNA having the transcription regulatory region and promoter region of the gene that encodes for the protein having L-amino acid transport, activity, possessed by the parent strain, for example, a nucleotide sequence 200 bp, preferably 100 bp upstream of the initiation codon of the protein, by subjecting the DNA to a mutation treatment in vitro, error-prone PCR or the like, after which the mutated DNA is replaced with the transcription regulatory region and promoter region of the gene that encodes for the protein having L-amino acid transport activity, present on the chromosomal DNA of the parent strain, before introduction of the mutation, using a publicly known method [Proc. Natl. Acad. Sci. USA., 97, 6640 (2000)] to prepare a modified strain having the mutated transcription regulatory region or promoter region, and the amounts transcribed of the genes that encode for the proteins having L-amino acid transport activity of the parent strain and the modified strain by RT-PCR, Northern hybridization or the like, or a method wherein the amounts produced of the proteins having L-amino acid transport activity of the parent strain and the modified strain are compared by SDS-PAGE or the like.

By replacing the promoter region of the gene that encodes for the protein having L-amino acid transport activity of the parent strain with a publicly known potent promoter sequence, it is also possible to obtain a microorganism wherein the amount produced of the protein having L-amino acid transport activity has been improved compared with the parent strain.

Such promoters include promoters derived from *Escherichia coli*, phage and the like, that function in *E. coli*, such as the trp promoter ($P_{trp}$), the lac promoter ($P_{lac}$), the $P_L$ promoter, the $P_R$ promoter, and the $P_{SE}$ promoter, the SPO1 promoter, the SPO2 promoter, the penP promoter and the like. Also included are promoters comprising two serially connected $P_{trp}$ units, artificially built promoters such as the tac promoter, the lacT7 promoter, and the let I promoter.

Furthermore, the xylA promoter [Appl. Microbiol. Biotechnol., 35, 594-599 (1991)] for expression in a microorganism belonging to the genus *Bacillus*, the P54-6 promoter [Appl. Microbiol. Biotechnol., 53, 674-679 (2000)] for expression in a microorganism belonging to the genus *Corynebacterium* and the like can also be used.

How to acquire a DNA that encodes for the protein having L-amino acid transport activity, and how to prepare a microorganism by transforming a parent strain with the DNA are described in detail.

(a) Acquisition of DNA that Encodes for the Protein Having L-Amino Acid Transport Activity A DNA that encodes for the protein having L-amino acid transport activity can be acquired by, for example, Southern hybridization of a chromosomal DNA library of a microorganism such as *E. coli* using a probe DNA that can be designed on the basis of the nucleotide sequence of a DNA that encodes for the protein having the amino acid sequence shown in any one of SEQ ID NOs:2, 4, 6 and 8, or PCR with the chromosomal DNA of a microorganism, preferably *E. coli*, as the template, using a primer DNA that can be designed on the basis of the nucleotide sequence [PCR Protocols, Academic Press (1990)].

A DNA that encodes for the protein having L-amino acid transport activity can also be acquired from the chromosomal DNA, cDNA library and the like of a microorganism having the nucleotide sequence of a DNA that encodes for the protein having the amino acid sequence shown in any one of SEQ ID NOs:2, 4, 6 and 8, by the above-described method, on the basis of the nucleotide sequence obtained by searching various gene sequence databases for a sequence having 80% or more, preferably 90% or more, more preferably 95% or more, still more preferably 97% or more, particularly preferably 98% or more, most preferably 99% or more homology, to the nucleotide sequence.

By integrating the DNA acquired, as it is or after being cleaved with an appropriate restriction enzyme and the like, into a vector by a conventional method, and introducing the recombinant DNA obtained into a host cell, then performing an analysis using a commonly used nucleotide sequence analytical method, for example, the dideoxy method [Proc. Natl. Acad. Sci., USA, 74, 5463 (1977)] or a nucleotide sequence analyzer such as the 3700 DNA analyzer (manufactured by Applied Biosystems Company), the nucleotide sequence of the DNA can be determined.

The vector is exemplified by pBluescriptII KS(+) (manufactured by Stratagene Company), pDIRECT [Nucleic Acids Res., 18, 6069 (1990)], pCR-Script Amp SK(+) (manufactured by Stratagene Company), pT7Blue (manufactured by Novagen Company), pCR II (manufactured by Invitrogen Company) and pCR-TRAP (manufactured by GenHunter Company) and the like.

Host cells include microorganisms belonging to the genus *Escherichia* and the like. Microorganisms belonging to the genus *Escherichia* include, for example, *E. coli* XL1-Blue, *E. coli* XL2-Blue, *E. coli* DH1, *E. coli* MC1000, *E. coli* ATCC 12435, *E. coli* W1485, *E. coli* JM109, *E. coli* HB101, *E. coli* No. 49, *E. coli* W3110, *E. coli* NY49, *E. coli* MP347, *E. coli* NM522, *E. coli* BL21, *E. coli* ME8415 and the like.

Any method of introducing a DNA into the host-cell can be used to introduce the recombinant DNA; examples include a method using the calcium ion [Proc. Natl. Acad. Sci., USA, 69, 2110 (1972)], the protoplast method (JP-A-SHO-63-248394), the electroporation method [Nucleic Acids Res., 16, 6127 (1988)] and the like.

If the determination of the nucleotide sequence shows the DNA acquired to be a partial-length DNA, the partial-length DNA may be subjected to Southern hybridization and the like to a chromosomal DNA library using a probe to acquire a full-length DNA.

Furthermore, the desired DNA can be also prepared by chemical synthesis on the basis of the nucleotide sequence of the determined DNA, using the model 8905 DNA synthesizer manufactured by Perceptive Biosystems Company and the like.

DNAs that can be acquired as described above include, for example, a DNA that encodes for the protein having the amino acid sequence shown in any one of SEQ ID NOS:2, 4, 6 and 8, and a DNA having the nucleotide sequence shown in any one of SEQ ID NOs:1, 3, 5 and 7.

(b) Acquisition of a Microorganism Transformed with a Plasmid Vector that Expresses a Protein Having L-Amino Acid Transport Activity On the basis of the DNA that encodes for the protein having L-amino acid transport activity, obtained by the method above(a), a DNA fragment of appropriate length comprising the portion that encodes for the protein having L-amino acid transport activity is prepared as necessary. By replacing a nucleotide in the nucleotide sequence of the portion that encodes for the protein having L-amino acid transport activity so as to be a most suitable codon for the expression in the host cell, a transformant wherein the amount of the protein has been improved can be acquired.

A recombinant DNA is prepared by inserting the DNA fragment downstream of the promoter of an appropriate expression vector.

By introducing the recombinant DNA into a host cell suitable for the expression vector, a transformant wherein the activity of a protein having L-amino acid transport activity has been improved compared with the host cell, that is, the parent strain, can be obtained.

Useful expression vectors include an expression vector that is capable of self-replication in the above-described host cell or can be integrated into the chromosome, and that comprises a promoter at a position where a DNA that encodes for the protein having L-amino acid transport activity can be transcribed.

When using a prokaryote as the host cell, the recombinant DNA having a DNA that encodes for the protein having L-amino acid transport activity is preferably a recombinant DNA that is capable of self-replication in the prokaryote, and is configured with a promoter, a ribosome-binding sequence, the DNA that encodes for the protein having L-amino acid transport activity, and a transcription termination sequence. A gene that controls the promoter may be contained.

Examples of expression vectors include pColdI (manufactured by Takara Bio Company), pCDF-1b, pRSF-1b (both manufactured by Novagen Company), pMAL-c2x (manufactured by New England Biolabs Company), pGEX-4T-1

(manufactured by GE Healthcare Bioscience Company), pTrcHis (manufactured by Invitrogen Company), pSE280 (manufactured by Invitrogen Company), pGEMEX-1 (manufactured by Promega Company), pQE-30 (manufactured by QIAGEN Company), pET-3 (manufactured by Novagen Company), pKYP10 (JP-A-SHO-58-110600), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescriptII SK(+), pBluescript II KS(−) (manufactured by Stratagene Company), pTrS30 [prepared from *Escherichia coli* JM109/pTrS30 (FERN BP-5407)], pTrS32 [prepared from *Escherichia coli* JM109/pTrS32 (FERN BP-5408)], pPAC31 (WO98/12343), pUC19 [Gene, 33, 103 (1985)], pSTV28 (manufactured by Takara Bio Company), pUC118 (manufactured by Takara Bio Company), pPA1 (JP-A-SHO-63-233798) and the like.

The promoter may be any one that functions in host cells such as of *E. coli*. Examples include promoters derived from *E. coli*, phage and the like, such as the trp promoter ($P_{trp}$), the lac promoter ($P_{lac}$), the $P_L$ promoter, the $P_R$ promoter, and the $P_{SE}$ promoter, as well as the SPO1 promoter, the SPO2 promoter, the penP promoter and the like. Promoters comprising two serially connected $P_{trp}$ units, artificially designed and modified promoters such as the tac promoter, the lacT7 promoter, and the let I promoter, and the like can also be used.

Furthermore, the xylA promoter for expression in a microorganism belonging to the genus *Bacillus* [Appl. Microbiol. Biotechnol., 35, 594-599 (1991)], the P54-6 promoter for expression in a microorganism belonging to the genus 10 *Corynebacterium* [Appl. Microbiol. Biotechnol., 53, 674-679 (2000)] and the like can also be used.

It is preferable to use a plasmid wherein the distance between the Shine-Dalgarno sequence, which is a ribosome-binding sequence, and the initiation codon is adjusted to an appropriate distance (for example, 6 to 18 bases).

In the recombinant DNA prepared by inserting a DNA that encodes for the protein having L-amino acid transport activity to an expression vector, a transcription termination sequence is not always necessary; however, it is preferable that a transcription termination sequence is arranged immediately downstream of the structural gene.

Such recombinant DNAs include, for example, pSnorM, pSemrD, pSrarD and pSeamA described below.

Hosts for the recombinant DNA include prokaryotes, more preferably bacteria.

Examples of the procaryote include microorganisms belonging to the genus *Escherichia*, the genus *Serratia*, the genus *Bacillus*, the genus *Brevibacterium*, the genus *Corynebacterium*, the genus *Microbacterium*, the genus *Pseudomonas*, the genus *Agrobacterium*, the genus *Alicyclobacillus*, the genus *Anabaena*, the genus *Anacystis*, the genus *Arthrobacter*, the genus *Azotobacter*, the genus *Chromatium*, the genus *Erwinia*, the genus *Methylobacterium*, the genus *Phormidium*, the genus *Rhodobacter*, the genus *Rhodopseudomonas*, the genus *Rhodospirillum*, the genus *Scenedesmus*, the genus *Streptomyces*, the genus *Synechoccus*, the genus *Zymomonas*, and the like, for example, *Escherichia coli, Bacillus subtilis, Bacillus megaterium, Bacillus amyloliquefaciens, Bacillus coagulans, Bacillus licheniformis, Bacillus pumilus, Brevibacterium ammoniagenes, Brevibacterium immariophilum, Brevibacterium saccharolyticum, Brevibacterium flavum, Brevibacterium lactofermentum, Corynebacterium glutamicum, Corynebacterium acetoacidophilum, Microbacterium ammoniaphilum, Serratia ficaria, Serratia fonticola, Serratia liquefaciens, Serratia marcescens, Pseudomonas aeruginosa, Pseudomonas putida, Agrobacterium radiobacter, Agrobacterium rhizogenes, Agrobacterium rubi, Anabaena cylindrical, Anabaena doliolum, Anabaena flos-aquae, Arthrobacter citreus, Arthrobacter globformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium sp. ATCC29409, Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Zymomonas mobilis* and the like. Examples of preferable procaryote include bacteria belonging to the genus *Escherichia*, the genus *Serratia*, the genus *Bacillus*, the genus *Brevibacterium*, the genus *Corynebacterium*, the genus *Pseudomonas* or the genus *Streptomyces*, for example, the above-mentioned species belonging to the genus *Escherichia*, the genus *Serratia*, the genus *Bacillus*, the genus *Brevibacterium*, the genus *Corynebacterium*, the genus *Pseudomonas* or the genus *Streptomyces*. Examples of more preferable bacteria include *Escherichia coli, Corynebacterium glutamicum, Corynebacterium ammoniagenes, Corynebacterium lactofermentum, Corynebacterium flavum, Corynebacterium efficiens, Bacillus subtilis, Bacillus megaterium, Serratia marcescens, Pseudomonas putida, Pseudomonas aeruginosa, Streptomyces coelicolor* and *Streptomyces lividans*, and particularly preferred is *Escherichia coli*.

(c) Acquisition of a Microorganism Wherein a DNA that Encodes For the Protein Having L-Amino Acid Transport Activity is Integrated in the Chromosomal DNA By integrating a DNA that encodes for the protein having L-amino acid transport activity, obtained by the method above (a), into an anywhere position in the chromosomal DNA, it is also possible to acquire a microorganism wherein the activity of the protein having L-amino acid transport activity is higher than that of the parent strain.

Methods for integrating a DNA that encodes for the protein having L-amino acid transport activity into an anywhere position in the chromosomal DNA of a microorganism include methods based on homologous recombination; when using *E. coli* as the host, that is, the parent strain, the method described in Proc. Natl. Acad. Sci. USA., 97, 6640 (2000) can be mentioned.

(2) Preparation of a Microorganism Having the Capability of Producing an L-Amino Acid The microorganism having the capability of producing an L-amino acid, used in the process for producing L-amino acid of the present invention may be any microorganism having the capability. When a strain isolated from nature itself has the capability, the microorganism may be the strain as it is; in case of a modified or transformed mutant strain, it may be a microorganism to which the capability of producing a desired L-amino acid is conferred artificially by a publicly known method and the like.

The publicly known method is exemplified by:
(a) methods wherein at least one mechanism behind the control of amino acid biosynthesis is mitigated or cancelled, (b) methods wherein the expression of at least one enzyme involved in amino acid biosynthesis is enhanced,
(c) methods wherein the number of copies of at least one enzyme gene involved in amino acid biosynthesis is amplified,
(d) methods wherein at least one metabolic pathway that branches from the biosynthesis pathway for an amino acid to a metabolite other than the amino acid is weakened or blocked, and
(e) methods wherein a cell strain whose resistance to amino acid analogues is higher than that of the wild-type strain is selected, and the like; the above-described publicly known methods can be used alone or in combination.

Methods above (a) are described in, for example, Agric. Biol. Chem., 43, 105-111 (1979), J. Bacteriol., 110, 761-763 (1972) and Appl. Microbiol. Biotechnol., 39, 318-323 (1993) and the like; methods (b) above are described in, for example, Agric. Biol. Chem., 43, 105-111 (1979) and J. Bacteriol., 110, 761-763 (1972) and the like; methods (c) above are described in, for example, Appl. Microbiol. Biotechnol., 39, 318-323 (1993) and Agric. Biol. Chem., 39, 371-377 (1987) and the like; methods (d) above are described in, for example, Appl. Environ. Micribiol., 38, 181-190 (1979) and Agric. Biol. Chem., 42, 1773-1778 (1978) and the like; methods (e) above are described in, for example, Agric. Biol. Chem., 36, 1675-1684 (1972), Agric. Biol. Chem., 41, 109-116 (1977), Agric. Biol. Chem., 37, 2013-2023 (1973) and Agric. Biol. Chem., 51, 2089-2094 (1987) and the like. With reference to the above-described documents and the like, microorganisms having the capability of producing various amino acids can be prepared.

Furthermore, regarding how to prepare a microorganism having the capability of producing an amino acid in any one of (a) to (e) above or a combination thereof, many examples are described in Biotechnology 2nd ed., Vol. 6, Products of Primary Metabolism (VCH Verlagsgesellschaft mbH, Weinheim, 1996), section 14a, 14b, Advances in Biochemical Engineering/Biotechnology, 79, 1-35 (2003), and Aminosan Hakko, Japan Scientific Societies Press, Hiroshi Aida et al. (1986); in addition to the above, many reports are available on specific methods of preparing a microorganism having the capability of producing an amino acid, including JP-A-2003-164297, Agric. Biol. Chem., 39, 153-160 (1975), Agric. Biol. Chem., 39, 1149-1153 (1975), JP-A-SHO-58-13599, J. Gen. Appl. Microbiol., 4, 272-283 (1958), JP-A-AHO-63-94985, Agric. Biol. Chem., 37, 2013-2023 (1973), pamphlet for International Patent Application Publication 97/15673, JP-A-SHO-56-18596, JP-A-SHO-56-144092, JP-T-2003-511086 and the like; with reference to the above-described documents and the like, a microorganism having the capability of producing one or more kinds of amino acids can be prepared.

Microorganisms having the capability of producing an amino acid, that can be prepared by one of the above-described method include, for example, microorganisms that lack the sdaA gene, the sdaB gene, the sdaC gene and the glyA gene, which possess L-serine degradation and uptake activities, and that exhibit enhanced expression of the serA gene deregulated to L-serine, as L-serine producers; microorganisms that lack the glnE gene as L-glutamine producers; microorganisms that carry the cysE gene deregulated to L-cysteine, for example, as L-cysteine producers; microorganisms that express the pheA gene deregulated to L-phenylalanine and/or the aroF gene deregulated to tyrosine and the like as L-phenylalanine producers, and microorganisms to which α-amino-β-hydroxyvalericacid (AHV) resistance and L-isoleucine, L-methionine and L-proline auxotrophy are conferred as L-threonine producers bacteria.

The above-described microorganism that produces and accumulates an amino acid may be any microorganism to which one of the methods (a) to (e) above is applicable, or any microorganism having the above-described genetic characters, and is preferably a prokaryote, more preferably a bacterium. Hosts for the recombinant DNA include prokaryotes, more preferably bacteria.

Specific examples of microorganisms that produce an amino acid include the *Escherichia coli* ATCC9637sdaABCglyA/pSserAfbr2 strain, which lacks L-serine degrading enzymes (sdaA, sdaB, glyA) and the uptake system (sdaC), and which carries an expression plasmid for the serA gene deregulated to L-serine, as an L-serine producer; *Escherichia coli* JGLE1 and *Escherichia coli* JGLBE1, which are described in the pamphlet for International Patent Application Publication 06/001379 or the pamphlet for US Patent Application Publication 2005-0287626, and the like, as L-glutamine producers; the *Escherichia coli* ATCC9637sdaABCcysE256/pScysEfbr1 strain, which lacks L-serine degrading enzymes (sdaA, sdaB) and the uptake system (sdaC), which has the cysE gene on the chromosomal DNA replaced with the cysE gene deregulated to L-cysteine, and which carries an expression plasmid for the cysE gene deregulated to L-cysteine, as an L-cysteine producer; the *Escherichia coli* NM522/pBpheAfbraroFfbr strain, which carries an expression plasmid for the pheA gene deregulated to L-phenylalanine and the aroF gene deregulated to L-tyrosine, and the like, as L-phenylalanine producers; ATCC21148, ATCC21277, ATCC21650 and the like as L-threonine producers.

Furthermore, specific examples of microorganisms having the capability of producing an amino acid include FERM BP-5807 and ATCC13032 as L-glutamic acid producers; FERM P-4806 and ATCC14751 as L-glutamine producers; FERM P-5084 and ATCC13286 as L-lysine producers; FERM P-5479, VKPM B-2175 and ATCC21608 as L-methionine producers; FERM BP-3757 and ATCC14310 as L-isoleucine producers; ATCC13005 and ATCC19561 as L-valine producers; FERM BP-4704 and ATCC21302 as L-leucine producers; FERM BP-4121 and ATCC15108 as L-alanine producers; ATCC21523 and FERM BP-6576 as L-serine producers; FERM BP-2807 and ATCC19224 as L-proline producers; FERM P-5616 and ATCC21831 as L-arginine producers; ATCC13232 as an L-ornithine producer; FERM BP-6674 and ATCC21607 as L-histidine producers; DSM10118, DSM10121, DSM10123 and FERM BP-1777 as L-tryptophan producers; ATCC13281 and ATCC21669 as L-phenylalanine producers; ATCC21652 as an L-tyrosine producer; W3110/pHC34 (described in JP-T-2003-511086) as an L-cysteine producer; *Escherichia coli* SOLR/pRH71 described in WO96/27669 as an L-4-hydroxyproline producer; FERM BP-5026 and FERMBP-5409 as L-3-hydroxyproline producers, and FERM P-5643 and FERM P-1645 as L-citrullin producers.

The microbial strains shown by the FERM numbers above can be obtained from the independent administrative corporation International Patent Organism Depositary, National Institute of Advanced Industrial Science and Technology (Japan); the microbial strains shown by the ATCC numbers from the American Type Culture Collection (US); the microbial strains shown by the VKPM numbers from the Russian National Collection of Industrial Microorganisms (Russia); and the microbial strains shown by the DSM numbers from Deutsche Sammlung von Mikroorganismen and Zellkulturen (Germany).

3. Manufacturing Process for L-Amino Acid of the Present Invention

A culture of a microorganism that can be prepared by the method described in above item 2 can be acquired by culturing the microorganism using a natural medium or synthetic medium that comprises a carbon source, a nitrogen source, minerals and the like that can be utilized by the microorganism, and that enables efficient cultivation of the transformant.

The carbon source may be any one that can be utilized by the organism; carbohydrates such as glucose, fructose, sucrose, molasses containing them, and starch or starch hydrolysates, organic acids such as acetic acid and propionic acid, alcohols such as ethanol and propanol and the like can be used.

Useful nitrogen sources include ammonia, ammonium salts of inorganic acids or organic acids such as ammonium chloride, ammonium sulfate, ammonium acetate, and ammonium phosphate, other nitrogen-containing compounds, as well as peptone, meat extract, yeast extract, corn steep liquor, casein hydrolysates, soy cake and soy cake hydrolysates, various fermented cell bodies, and digests thereof, and the like.

Useful inorganic salts include primary potassium phosphate, secondary potassium phosphate, magnesium phosphate, magnesium sulfate, sodium chloride, ferrous sulfate, manganese sulfate, copper sulfate, calcium carbonate and the like.

The cultivation is normally performed under aerobic conditions such as shaking culture or deep spinner culture. Cultivation temperature is preferably 15 to 40° C.; cultivation time is normally 5 hours to 7 days. During the cultivation, pH is kept at 3.0 to 9.0. Adjustments of the pH are achieved using an inorganic or organic acid, an alkali solution, urea, calcium carbonate, ammonia, and the like.

Antibiotics such as ampicillin and tetracycline may be added to the medium during the cultivation as necessary.

When culturing a microorganism transformed with an expression vector using an inducible promoter, an inducer may be added to the medium as necessary. For example, when culturing a microorganism transformed with an expression vector using the lac promoter, isopropyl-β-D-thiogalactopyranoside and the like may be added; when culturing a microorganism transformed with an expression vector using the trp promoter, indolacrylic acid and the like may be added to the medium.

The transformant of a microorganism having the capability of producing an L-amino acid, and expressing a protein having L-amino acid transport activity, constructed as described above, is cultured in a medium to produce an L-amino. The L-amino acid produced is efficiently transported from inside of the cell body into the medium by the L-amino acid transport activity possessed by the transformant, and accumulates in the medium. Therefore, by collecting the L-amino from the culture, the desired L-amino can be efficiently produced.

Collection of the L-amino accumulated in the aqueous medium or culture can be achieved by an ordinary method using activated charcoal, ion exchange resin or the like or by organic solvent extraction, crystallization, thin-layer chromatography, high performance liquid chromatography and the like.

Amino acid producing strains were prepared by the methods described below.

[1] Construction an Expression Plasmid for Deregulated Sera Gene

PCR was performed with the chromosomal DNA of the *Escherichia coli* W3110 strain as the template, using synthetic DNAs consisting of the nucleotide sequences shown in SEQ ID NOS:18 and 19, respectively, as a primer set. The PCR was carried out by preparing 50 μL of a reaction liquid comprising 0.1 μg of the chromosomal DNA as the template, 0.3 μmol/L of each primer, 1 unit of KOD-plus-DNA polymerase (manufactured by Toyobo), 5 μL of ×10 buffer solution for KOD-plus-DNA polymerase (manufactured by Toyobo), 100 μmol/L MgSO$_4$, and 200 μmol/L of each dNTP (dATP, dGTP, dCTP and dTTP), and repeating the step of treatment at 94° C. for 15 seconds, at 55° C. for 30 seconds, and at 68° C. for 2 minutes 30 times.

The amplified DNA fragment obtained by the PCR was digested with BglII and HindIII, and pTrs30 with BamHI and HindIII, after which the two DNAs were ligated together using a ligation kit (manufactured by Takara Bio Company), and the *Escherichia coli* DH5α strain was transformed using the ligation product DNA. By the method described above, a plasmid DNA wherein the serA gene was joined downstream of the trp promoter was acquired, and this was named as pTrs30-serA.

PCR was performed with pTrs30-serA as the template, using synthetic DNAs consisting of the nucleotide sequences shown in SEQ ID NOS:20 and 21, respectively, whose 5' terminus was modified with a phosphate group, as a primer set.

The PCR reaction was carried out with the same conditions and reaction liquid composition as the above but using 0.01 μg of pTrs30-serA DNA as the template.

After the PCR reaction, amplification of an about 5.8 kb DNA fragment was confirmed; the amplified DNA fragment was purified according to a conventional method.

The linear DNA fragments amplified above were ligated together into a circular using a ligation kit (manufactured by Takara Bio Company); the *Escherichia coli* DH5α strain was transformed using the circular DNA. With ampicillin resistance as an index, a transformant was selected; plasmid DNA was extracted from the transformant obtained.

Thus, a plasmid DNA having a structure wherein the serA gene deregulated to L-serine, resulting from replacement of the 294th glycine in the amino acid sequence shown in SEQ ID NO:17 by L-valine, was inserted downstream of the trp promoter of pTrs30, was prepared, and this was named as pSserAfbr1.

Furthermore, PCR was performed with pSserAfbr1 as the template using synthetic DNAs consisting of the nucleotide sequences shown in SEQ ID NOS:22 and 23, respectively, whose 5' terminus was modified with a phosphate group, as a primer set.

The PCR reaction liquid composition and reaction conditions were the same as those described above.

The amplified linear DNA fragments were ligated together into a circular DNA, and the *Escherichia coli* DH5α strain was transformed using the circular DNA. Plasmid DNA was extracted from the transformant obtained.

Thus the plasmid DNA having the structure wherein the serA gene deregulated to L-serine, resulting from replacement of the 294th glycine in the amino acid sequence shown in SEQ ID NO:17 by L-valine, and the 364th L-asparagine by L-alanine, was inserted downstream of the trp promoter of pTrs30, was prepared. this was named as pSserAfbr2.

[2] Preparation of Microorganisms Lacking the sdaA, sdaB, sdaC And glyA Genes

Deletion of a particular gene on the chromosomal DNA of *Escherichia coli* was performed according to a method utilizing a homologous recombination system of lambda phage [Proc. Natl. Acad. Sci. USA., 97, 6641-6645 (2000)]. The plasmids pKD46, pKD3 and pCP20 described below were used after being extracted by a publicly known method from Escherichia coli strains carrying the plasmids, obtained from the Escherichia coli Genetic Stock Center (Yale University, US).

(1) Cloning of Drug Resistance Gene Fragments for Gene Deletion

PCR was performed using DNAs consisting of the nucleotide sequences shown in SEQ ID NOS:24 and 25, and 26 and 27, respectively, as a primer set for amplifying a DNA fragment for deleting the sdaA gene, DNAs consisting of the nucleotide sequences shown in SEQ ID NOS:28 and 29, and 30 and 31, respectively, as a primer set for amplifying a DNA fragment for deleting the sdaC-sdaB gene, and DNAs consisting of the nucleotide sequences shown in SEQ ID NOS:32 and 33, and 34 and 35, respectively, as a primer set for amplifying a DNA fragment for deleting the glyA gene, with the chromosomal DNA of the Escherichia coli ATCC9637 strain as the template. The PCR was carried out by repeating the step of treatment at 94° C. for 1 minute, at 55° C. for 2 minutes, and at 72° C. for 1 minute 30 times using 40 µL of a reaction liquid comprising 0.1 µg of the chromosomal DNA, 0.5 µmol/L of each primer, 2.5 units of Pfu DNA polymerase, 4 µL of ×10 buffer solution for Pfu DNA polymerase, and 200 µmol/L of each deoxyNTP.

By the PCR, desired homologous sequence fragments of upstream and downstream regions for deleting each of the sdaA, sdaB, sdaC and glyA genes (referred to as upstream DNA fragment and downstream DNA fragment, respectively) were acquired.

Next, by a crossover PCR method [J. Bacteriol., 179, 6228-6237 (1997)] with the upstream DNA fragment and downstream DNA fragment of each of the above-described genes, and HindIII-cleaved pKD3 as the template, using a synthetic DNA consisting of the nucleotide sequences shown in SEQ ID NOS24 and 27, respectively, as a primer set for the DNA fragment for deleting the sdaA gene, or using synthetic DNAs consisting of the nucleotide sequences shown in SEQ ID NOS:28 and 31, respectively, as a primer set for the DNA fragment for deleting the sdaC-sdaB gene, or using a synthetic DNA consisting of the nucleotide sequences shown in SEQ ID NOS:32 and 35, respectively, as a primer set for the DNA fragment for deleting the glyA gene, a DNA fragment comprising the chloramphenicol resistance gene portion of pKD3 inserted into the center, and the three DNA fragments joined together (DNA fragments for deleting the sdaA, sdaB, sdaC and glyA genes) was acquired.

(2) Preparation of Escherichia coli Lacking the sdaA Gene

The Escherichia coli ATCC9637 strain was transformed with pKD46; the transformant obtained was named as Escherichia coli ATCC9637/pKD46.

The DNA fragment for deleting the sdaA gene, acquired by method above, was introduced by the electroporation into Escherichia coli ATCC9637/pKD46 obtained by cultivation in the presence of 10 mmol/L L-arabinose and 50 µg/ml ampicillin; with chloramphenicol resistance as the index, a transformant wherein the DNA fragment was integrated on the chromosomal DNA of Escherichia coli ATCC9637/pKD46 by homologous recombination (the transformant was named as Escherichia coli ATCC9637/pKD46 sdaA::cat) was selected.

Escherichia coli ATCC9637/pKD46 sdaA::cat was inoculated to a LB agar medium [LB medium [10 g/l Bactotrypton (manufactured by Difco Company), 5 g/l yeast extract (manufactured by Difco Company), 5 g/l sodium chloride] supplemented with 1.5% agar] containing 25 mg/L chloramphenicol, and cultured at 42° C. for 14 hours, after which single colony was isolated. Each colony obtained was replicated to a LB agar medium containing 25 mg/L chloramphenicol and a LB agar medium containing 100 mg/l ampicillin, and cultured at 37° C.; with chloramphenicol resistance and ampicillin susceptibility as the index, a strain deprived of pKD46 (Escherichia coli ATCC9637 sdaA::cat) was selected.

Next, Escherichia coli ATCC9637 sdaA::cat was transformed with pCP20 to acquire a strain carrying pCP20 (Escherichia coli ATCC9637/pCP20 sdaA::cat).

Escherichia coli ATCC9637/pCP20 sdaA::cat was inoculated to a drug-free LB agar medium, and cultured at 42° C. for 14 hours, after which single colony was isolated. Each colony obtained was replicated to a drug-free LB agar medium, a LB agar medium containing 25 mg/L chloramphenicol, and a LB agar medium containing 100 mg/L ampicillin, and cultured at 30° C.; several strains exhibiting chloramphenicol susceptibility and ampicillin susceptibility were selected.

The chromosomal DNA was prepared from each of the strains selected above; PCR was performed using DNAs designed on the basis of the nucleotide sequences of DNAs located outside of the sdaA gene on the chromosomal DNA as a primer set, with the chromosomal DNA as the template. The PCR was carried out by repeating the step consisting of treatment at 94° C. for 1 minute, at 55° C. for 2 minutes, and at 72° C. for 3 minutes 30 times using 40 µL of a reaction liquid comprising 0.1 g of the chromosomal DNA, 0.5 µmol/L of each primer, 2.5 units of Pfu DNA polymerase, 4 µL of ×10 buffer solution for Pfu DNA polymerase, and 200 µmol/L of each deoxyNTP.

A strain confirmed to lack the sdaA gene from the chromosomal DNA by the above-described PCR was named as the Escherichia coli ATCC9637sdaA strain.

(3) Preparation of Escherichia coli Multiply Lacking the sdaA, sdaB, sdaC and glyA Genes By repeating the method performed in (2) on the ATCC9637sdaA strain obtained in (2), using the chloramphenicol resistance gene fragment for deleting the sdaC-sdaB or glyA gene, acquired in (1), a strain further lacking the sdaC, sdaB and glyA genes was prepared.

Acquisition of a strain lacking the genes by the above-described method was confirmed by preparing the chromosomal DNA from each selected strain in the same manner as (2), and performing PCR using DNAs designed on the basis of the nucleotide sequences of DNAs located outside of the sdaC-sdaB or glyA gene on the chromosomal DNA as a primer set, with the chromosomal DNA as the template.

The strain identified as a strain multiply lacking the sdaA, sdaC-sdaB and glyA genes above was named as the Escherichia coli ATCC9637sdaABCglyA strain.

[3] Construction of Escherichia coli-Derived Expression Plasmid for Deregulated pheA Gene and Deregulated aroF Gene (1) Building an Expression Plasmid for Deregulated pheA Gene A deregulated pheA gene was acquired from the plasmid pE pheA 22 (JP-A-SHO-61-260892), which expresses the pheA gene deregulated to phenylalanine, obtained by introduction of a phenylalanine analogue resistance mutation, and a deregulated aroF gene was acquired from the plasmid pE aroF 18 (JP-A-SHO-62-65691), which expresses the aroF gene deregulated to tyrosine, obtained by introduction of a tyrosine resistance mutation; an expression plasmid was constructed by the method described below.

PCR was performed using synthetic DNAs having the nucleotide sequences shown in SEQ ID NOS:36 and SEQ ID NO:37, respectively, as a primer set, with the plasmid pE pheA 22 as the template. The PCR was carried out by preparing 40 µL of a reaction liquid comprising 10 ng of plasmid DNA, 0.5 μmol/L of each primer, 2.5 units of Pfu DNA polymerase, 4 μL of ×10 buffer solution for Pfu DNA polymerase, and 200 μmol/L of each dNTP, and repeating the step consisting of treatment at 94° C. for 1 minute, at 55° C. for 2 minutes, and at 72° C. for 3 minutes 30 times.

A 1/10 volume of the reaction liquid was subjected to agarose gel electrophoresis, and amplification of an about 1.1 kb fragment corresponding to a pheA gene fragment was confirmed, after which TE-saturated phenol/chloroform in a volume equal to that of the remaining reaction liquid was added, and they were mixed. The mixed liquid was centrifuged, after which a 2-fold volume of cold ethanol was added to, and mixed with, the upper layer obtained, and the mixture was allowed to stand at −80° C. for 30 minutes. The solution was centrifuged, and the precipitate of DNA obtained was dissolved in 20 μL of TE.

Using 5 μL of the solution, the amplified DNA was cleaved with the restriction enzymes ClaI and BamHI; DNA fragments were separated by agarose gel electrophoresis, after which a 1.1 kb DNA fragment comprising the pheA gene was recovered using the Gene Cleaning II kit.

A 0.2 μg of the expression vector pTrS30 comprising the trp promoter was cleaved with the restriction enzymes ClaI and BamHI, after which DNA fragments were separated by agarose gel electrophoresis, and a 4.6 kb DNA fragment was recovered in the same manner as the above.

The 1.1 kb DNA fragment comprising the pheA gene and the 4.6 kb DNA fragment, obtained above, were ligated by a reaction at 16° C. for 16 hours using a ligation kit.

The *Escherichia coli* NM522 strain was transformed using the reaction liquid by a method using the calcium ion, after which the transformant was applied over a LB agar medium supplemented with 50 μg/ml ampicillin, and cultured at 30° C. overnight.

A plasmid was extracted from a colony of transformants that had grown according to a publicly known method; an expression plasmid for the deregulated pheA gene was confirmed to be acquired by restriction enzyme digestion, and the plasmid was named as pPHEA1.

(2) Construction of Expression Plasmid for Deregulated pheA Gene and Deregulated aroF Gene PCR was performed using synthetic DNAs having the nucleotide sequences shown in SEQ ID NOS:38 and SEQ ID NO:39, respectively, as a primer set, with the plasmid pE aroF 18 as the template. The PCR was carried out using the same reaction liquid composition and reaction conditions as above (1).

A 1/10 volume of the reaction liquid was subjected to agarose gel electrophoresis, and amplification of an about 1.1 kb fragment corresponding to an aroF gene fragment was confirmed, after which TE-saturated phenol/chloroform in a volume equal to that of the remaining reaction liquid was added, and they were mixed. The mixed liquid was centrifuged, after which a 2-fold volume of cold ethanol was added to, and mixed with, the upper layer obtained, and the mixture was allowed to stand at −80° C. for 30 minutes. The solution was centrifuged, and the precipitate of DNA obtained was dissolved in 20 μL of TE.

Using 5 μL of the solution, the amplified DNA was cleaved with the restriction enzymes BglII and BamHI, and DNA fragments were separated by agarose gel electrophoresis, after which a 1.1 kb DNA fragment comprising the deregulated aroF gene was recovered using the Gene Clean II kit.

Next, 0.2 μg of the expression plasmid pPHEA1 for deregulated pheA gene obtained in above(1) was cleaved with the restriction enzyme BamHI, after which DNA fragments were separated by agarose gel electrophoresis, and a 5.7 kb DNA fragment was recovered in the same manner as the above. Terminal dephosphorylation of the 5.7 kb DNA fragment was performed by alkaline phosphatase treatment at 60° C. for 30 minutes. TE-saturated phenol/chloroform in a volume equal to that of the reaction liquid was added, and they were mixed; the mixture was centrifuged, after which a 2-fold volume of cold ethanol was added to, and mixed with, the upper layer obtained, and the mixture was allowed to stand at −80° C. for 30% minutes. The solution was centrifuged, and the precipitate of DNA obtained was dissolved in 20 μL of TE.

The 1.1 kb DNA fragment comprising the deregulated aroF gene and the alkaline phosphatase-treated 5.7 kb DNA fragment, obtained above, were ligated together by a reaction at 16° C. for 16 hours using a ligation kit.

The *Escherichia coli* NM522 strain was transformed using the reaction liquid by a method using the calcium ion, after which the reaction liquid was applied to an LB agar medium containing 50 μg/mL ampicillin, and cultured at 30° C. overnight.

A plasmid was extracted from a colony of transformants that had grown, according to a publicly known method; an expression plasmid for a deregulated aroF gene and a deregulated pheA gene wherein the deregulated aroF gene was inserted in the orthodox orientation with respect to the deregulated pheA gene was confirmed to be acquired by restriction enzyme digestion, and the plasmid was named as pBpheAfbraroFfbr.

[4] Preparation of a Microorganism Lacking the Serine Decomposition and Uptake System sdaA, sdaB, and sdaC Genes, and Having a Deregulated cysE Gene Replacing on the Chromosome (1) Cloning of a Drug Resistance Gene Fragment for Deleting the cysE Gene and a Gene Fragment for Replacing a Deregulated cysE gene PCR was performed in the same manner as in [2] (1) and using synthetic DNAs consisting of the nucleotide sequences shown in SEQ ID NOS:40 and 41, and by SEQ ID NOS:42 and 43, respectively, as a primer set for amplifying a DNA fragment for deleting the cysE gene, with the chromosomal DNA of the *Escherichia coli* W3110 strain as the template. By the PCR, desired homologous sequence fragments of upstream and downstream regions for deleting the cysE gene (referred to as upstream DNA fragment and downstream DNA fragment, respectively) were acquired.

PCR was performed in the same manner as the above using synthetic DNAs consisting of the nucleotide sequences shown in SEQ ID NOs:40 and 44, respectively, as well as synthetic DNAs consisting of the nucleotide sequences shown in SEQ ID NOS:43 and 45, respectively, each as a primer set for amplifying a DNA fragment for replacing the deregulated cysE gene, with the chromosomal DNA of the *Escherichia coli* W3110 strain as the template, to acquire homologous sequence fragments of upstream and downstream regions for replacing deregulated cysE (referred to as replacement upstream DNA fragment and replacement downstream DNA fragment, respectively).

Next, to acquire a DNA fragment for deleting the cysE gene, crossover PCR was performed with the upstream DNA fragment and downstream fragment for deleting the cysE gene, obtained above, and HindIII-cleaved pKD3 as the template, with DNAs consisting of the nucleotide sequences shown in SEQ ID NOS:40 and 43, respectively, as a primer set, to acquire a DNA fragment wherein the chloramphenicol resistance gene portion of pKD3 was inserted into the central portion, and the three DNA fragments are joined.

To acquire a DNA fragment for replacing a deregulated cysE gene, crossover PCR was performed with the above-described replacement upstream DNA fragment and replacement downstream DNA fragment as the template, using DNAs consisting of the nucleotide sequences shown in SEQ ID NOS:40 and 43, respectively, as a primer set; thereby, a DNA fragment wherein the two DNA fragments comprising a desensitization mutation were joined on the cysE gene was acquired.

(2) Preparation of *Escherichia coli* Having a Replacing Deregulated cysE Gene

The *Escherichia coli* ATCC9637sdaABC strain lacking the sdaA, sdaB, and sdaC genes, obtained in [2] (3), was transformed with pKD46; the transformant obtained was named as *Escherichia coli* ATCC9637sdaABC/pKD46.

In the same manner as [2] (2), transformants wherein the DNA fragment for deleting the cysE gene of above (1) was integrated on the chromosomal DNA of *Escherichia coli* ATCC9637sdaABC/pKD46 by homologous recombination (*Escherichia coli* ATCC9637sdaABC/pKD46 cysE::cat) were selected, after which strains deprived of the chloramphenicol resistance gene was selected.

The chromosomal DNA was prepared from each of the strains selected above, and PCR was performed in the same manner as [2] (2) using DNAs designed on the basis of the nucleotide sequences of the DNA located outside of the cysE gene on the chromosomal DNA as a primer set.

The strain that provided a short amplified fragment not containing the cysE gene in the above-described PCR was selected as a strain lacking the cysE gene, and was named as the *Escherichia coli* ATCC9637sdaABCcysE1 strain.

Next, the deregulated cysE gene was replaced on the chromosome.

The above-described *Escherichia coli* ATCC9637sdaABCcysE1 strain was transformed with pKD46; the transformant obtained was named as *Escherichia coli* ATCC9637sdaABCcysE1/pKD46.

In the same manner as [2] (2), transformants wherein the DNA fragment for replacing the deregulated cysE gene of above (1) was integrated on the chromosomal DNA of *Escherichia coli* ATCC9637sdaABCcysE1/pKD46 by homologous recombination were selected on the basis of growth on the M9+glucose minimal agar medium [6 g/L disodium hydrogen phosphate, 3 g/L potassium dihydrogen phosphate, 0.5 g/L sodium chloride, 1 g/L ammonium chloride, 2 g/L glucose, 1 mM magnesium sulfate heptahydrate, 0.1 mM calcium chloride dihydrate, 10 mg/l vitamin $B_1$, and agar 15 g/L, of which glucose, magnesium sulfate, calcium chloride, and vitamin $B_1$ were separately sterilized and added].

The chromosomal DNA was prepared from each of the strains selected above, and PCR was performed in the same manner as [2] (2) using DNAs designed on the basis of the nucleotide sequences of the DNA located outside of the cysE gene on the chromosomal DNA as a primer set.

As a DNA fragment comprising the cysE gene was amplified in the above-described PCR, acquirement of a strain having replacement with the deregulated cysE gene was confirmed, and this was named the *Escherichia coli* ATCC9637sdaABCcysE256 strain.

[5] Construction of *Escherichia coli*-Derived Expression Plasmid for Deregulated cysE Gene The *Escherichia coli* ATCC9637sdaABCcysE256 strain obtained in [4] was inoculated to a LB medium and subjected to standing culture at 30° C. overnight. After the cultivation, the chromosomal DNA of the microorganism was isolated and purified by the method using saturated phenol described in the Current Protocols in Molecular Biology.

With the same conditions and reaction liquid composition as those in [1], PCR was performed using synthetic DNAs consisting of the nucleotide sequences shown in SEQ ID NOS:46 and 47, respectively, as a primer set, and using the above-described chromosomal DNA as the template.

The amplified DNA fragment obtained by the above-described PCR and pTrs30 were digested with HindIII and BamHI, respectively, after which the two DNAs were ligated together using a ligation kit (manufactured by Takara Bio Company), and the *Escherichia coli* DH5α strain was transformed using the ligation product DNA. Plasmid DNA was extracted from the transformant obtained.

An expression vector wherein the deregulated cysE gene was joined downstream of the trp promoter was built by the method described above, and was named as pScysEfbr1.

EXAMPLES

Examples of the present invention are given below, to which, however, the invention is not limited.

Example 1

(1) Construction of an Expression Plasmid for the norM Gene

PCR was performed with the chromosomal DNA of the *Escherichia coli* W3110 strain as the template, using synthetic DNAs consisting of the nucleotide sequences shown in SEQ ID NOS:9 and 10, respectively, as a primer set.

The PCR was carried out by preparing 50 μL of a reaction liquid comprising 0.1 μg of the chromosomal DNA as the template, 0.3 μmol/L of each primer, 1 unit of KOD-plus-DNA polymerase (manufactured by Toyobo), 5 μL of ×10 buffer solution for KOD-plus-DNA polymerase (manufactured by Toyobo), 100 μmol/L $MgSO_4$, and 200 μmol/L of each dNTP(dATP, dGTP, dCTP and dTTP), and repeating the step of treatment at 94° C. for 15 seconds, at 55° C. for 30 seconds, and at 68° C. for minutes 30 times.

Amplification of an about 1.4 kb DNA fragment was confirmed, and the DNA fragment was purified according to a conventional method.

The DNA fragment and the expression vector pTrs30 [can be prepared from *Escherichia coli* JM109/pTrS30 (FERM BP-5407)] were cleaved with HindIII and BamHI, respectively; DNA fragments were separated by agarose electrophoresis, after which each of the restriction enzyme digested DNA fragments was recovered using the GENECLEAN II kit (manufactured by BIO 101 Company).

The about 1.4 kb DNA fragment and pTrs30 restriction enzyme digested fragment obtained by the recovery were ligated together using a ligation kit (manufactured by Takara Bio Company).

The *Escherichia coli* DH5α strain (manufactured by Toyobo) was transformed using the DNA after the ligation; a transformant was selected with ampicillin resistance as an index.

A plasmid was extracted from the transformant selected, according to a publicly known method, and the structure thereof was analyzed using restriction enzymes; it was confirmed that the plasmid obtained had a structure wherein the norM gene consisting of the nucleotide sequence shown in SEQ ID NO:1 was inserted downstream of the trp promoter of the expression vector pTrS30. The plasmid was named as pTrs30-norM.

The plasmid pTrs30-norM and the expression vector pSTV29 (manufactured by Takara Bio Company) were cleaved with EcoRI and BamHI, respectively, and fragments were ligated together in the same manner as the above to yield a plasmid DNA having a structure wherein the trp promoter and the norM gene were inserted into pSTV29. The plasmid obtained was named pSnorM.

(2) Construction of an emrD Gene Expression Plasmid

With the same reaction liquid composition and reaction conditions as (1), PCR was performed with the chromosomal DNA of the *Escherichia coli* W3110 strain as the template, using synthetic DNAs consisting of the nucleotide sequences shown in SEQ ID NOS:11 and 12, respectively, as a primer set.

The amplified DNA fragment obtained by the PCR and pTrs30 were digested with HindIII and SacI, respectively, after which a plasmid DNA having a structure wherein the emrD gene consisting of the nucleotide sequence shown in SEQ ID NO:3 was inserted downstream of the trp promoter of pTrs30 was acquired in the same manner as (1). This plasmid DNA obtained was named as pTrs30-emrD.

The pTrs30-emrD and pSTV29 obtained above were digested with EcoRI and SacI, respectively, after which a plasmid DNA wherein the trp promoter and emrD gene were ligated together to pSTV29 was prepared in the same manner as (1). The plasmid DNA obtained was named as pSemrD.

(3) Construction of an rarD Gene Expression Plasmid

With the same reaction liquid composition and reaction conditions as (1), PCR was performed with the chromosomal DNA of the *Escherichia coli* W3110 strain as the template, using synthetic DNAs consisting of the nucleotide sequences shown in SEQ ID NOS:13 and 14, respectively, as a primer set.

The amplified DNA fragment obtained by the PCR and pTrs30 were digested with HindIII and BamHI, respectively, after which a plasmid DNA having a structure wherein the rarD gene consisting of the nucleotide sequence shown in SEQ ID NO:5 was inserted downstream of the trp promoter of pTrs30 was prepared in the same manner as (1), and this was named as pTrs30-rarD.

The pTrs30-rarD and pSTV29 obtained above were digested with EcoRI and BamHI, respectively, after which a plasmid DNA wherein the trp promoter and the rarD gene were ligated to pSTV29 was constructed in the same manner as (1), and this was named as pSrarD.

(4) Construction of an eamA Gene Expression Plasmid

With the same reaction liquid composition and reaction conditions as (1), PCR was performed with the chromosomal DNA of the *Escherichia coli* W3110 strain as the template, using synthetic DNAs consisting of the nucleotide sequences shown in SEQ ID NOS:15 and 16, respectively, as a primer set.

The amplified DNA fragment obtained by the PCR and pTrs30 were digested with HindIII and BamHI, respectively, after which a plasmid having a structure wherein the eamA gene consisting of the nucleotide sequence shown in SEQ ID NO:7 was inserted downstream of the trp promoter of pTrs30 was prepared in the same manner as (1), and this was named as pTrs30-eamA.

The pTrs30-eamA and pSTV29 obtained above were digested with EcoRI and BamHI, respectively, after which a plasmid DNA to having a structure wherein the trp promoter and the eamA gene were inserted into pSTV29 was prepared in the same manner as (1), and this was named as pSeamA.

Example 2

Production of L-serine (L-Ser)

The ATCC9637sdaABCglyA strain obtained in Preparation of Amino Acid Producers [2] was transformed with the pSserAfbr2 obtained in Preparation of Amino Acid Producers [1] to acquire *Escherichia coli* ATCC9637sdaABCglyA/pSserAfbr2, which has the capability of producing a protein possessing L-serine biosynthesis intermediate (3-phosphohydroxy-pyruvate) synthetase activity.

Next, *Escherichia coli* ATCC9637sdaABCglyA/pSserAfbr2 was transformed with each of pSnorM, pSemrD, pSrarD, pSeamA and pSTV29 obtained in Preparation of Amino Acid Producers [1] to acquire transformants, which were named as *Escherichia coli* ATCC9637sdaABCglyA/pSserAfbr2/pSnorM, ATCC9637sdaABCglyA/pSserAfbr2/pSemrD, ATCC9637sdaABCglyA/pSserAfbr2/pSrarD, ATCC9637sdaABCglyA/pSserAfbr2/pSeamA and ATCC9637sdaABCglyA/pSserAfbr2/pSTV29, respectively.

The transformant obtained above was inoculated to a large test tube containing 5 ml of the medium A [10 g/L Tripton (Difco), 5 g/L Yeast extract (Difco), 5 g/L sodium chloride, 1 g/L potassium dihydrogen phosphate, 3 g/L dipotassium hydrogen phosphate] supplemented with 100 μg/ml ampicillin and 20 μg/ml chloramphenicol, and cultured at 30° C. for 16 hours.

The culture broth was inoculated at 10% to a test tube containing 5 ml of the medium B [0.72 g/L Yeast extract, 14.4 g/L ammonium sulfate, 1.8 g/L magnesium sulfate heptahydrate, 72 mg/L calcium chloride, 100 μg/L vitamin $B_1$, 21.6 mg/L iron sulfate heptahydrate, 7.2 mg/L manganese sulfate, 1.4 mg/L copper sulfate, 3.6 mg/L zinc sulfate, 1.4 mg/L nickel chloride, 1.4 mg/L cobalt chloride, 21.6 mg/L calcium pantothenate, 14.4 mg/L nicotinic acid, 36 mg/L thiamine, 14.4 mg/L pyridoxine hydrochloride, 72 mg/L glycine, 21 g/L calcium carbonate, 48 g/L glucose, 0.56 g/L potassium dihydrogen phosphate, 2.88 g/L dipotassium hydrogen phosphate, 0.6 g/L disodium hydrogen phosphate; pH not adjusted; glucose, potassium dihydrogen phosphate, dipotassium hydrogen phosphate, and disodium hydrogen phosphate were added after being separately boiled] supplemented with 100 μg/ml ampicillin and 20 μg/ml chloramphenicol, and cultured at 30° C. for 24 hours, after which the culture broth was centrifuged, and a culture supernatant was acquired.

The products in the culture supernatant were analyzed using HPLC. The results are shown in Table 1.

TABLE 1

| E. coli strain | $OD_{660}$ | L-Ser (mg/L) |
|---|---|---|
| ATCC9637sdaABCglyA/pSserAfbr2/pSTV29 | 6.1 | 10.6 |
| ATCC9637sdaABCglyA/pSserAfbr2/pSnorM | 5.8 | 14.4 |
| ATCC9637sdaABCglyA/pSserAfbr2/pSemrD | 7.1 | 12.3 |
| ATCC9637sdaABCglyA/pSserAfbr2/pSrarD | 6.2 | 23.8 |
| ATCC9637sdaABCglyA/pSserAfbr2/pSeamA | 6.7 | 14.4 |

As shown in Table 1, each expression plasmid carrying the norM gene (shown in SEQ ID NO:1; hereinafter denoted in SEQ ID NO alone), the emrD gene (SEQ ID NO:3), the rarD gene (SEQ ID NO:5), or the eamA gene (SEQ ID NO:7) was introduced to increase the amount of expression of norM protein (SEQ ID NO:2), emerD protein (SEQ ID NO:4), rarD protein (SEQ ID NO:6) or eamA protein (SEQ ID NO:8), respectively; as a result, in all cases, the amount of L-serine accumulated in the medium increased.

Example 3

Production of L-glutamine (L-Gln)

The JGLE1 strain (pamphlet for International Patent Application Publication 06/001380, pamphlet for US Patent Application Publication 2008-0038786), which is a publicly known L-glutamine producer, was transformed with each of pSnorM, pSrarD and pSTV29 obtained in Preparation of Amino is Acid Producers [1]; the transformants obtained were named as *Escherichia coli* JGLE1/pSnorM, JGLE1/pSrarD and JGLE1/pSTV29, respectively.

Each transformant obtained above was inoculated to a large test tube containing 8 ml of a LB medium supplemented with 20 µg/ml chloramphenicol, and cultured at 30° C. for 16 hours.

The culture broth was inoculated at 1% to a test tube containing 8 ml of the medium C [16 g/L dipotassium hydrogen phosphate, 14 g/L potassium dihydrogen phosphate, 2 g/L ammonium sulfate, 1 g/L citric acid (anhydrous), 1 g/L casamino acid (manufactured by Difco Company), 10 g/L glucose, 10 mg/L vitamin $B_1$, 2 g/L magnesium sulfate heptahydrate, 10 mg/L manganese sulfate pentahydrate, 50 mg/L iron sulfate heptahydrate, 100 mg/L L-proline; adjusted to pH 7.2 with 10 mol/L sodium hydroxide; glucose, vitamin $B_1$, magnesium sulfate heptahydrate, manganese sulfate pentahydrate, iron sulfate heptahydrate, and L-proline were added separately after being boiled] supplemented with 20 µg/ml chloramphenicol, and cultured at 30° C. for 24 hours, after which the culture broth was centrifuged, and a culture supernatant was acquired.

The products in the culture supernatant were analyzed using HPLC. The results are shown in Table 2.

TABLE 2

| E. coli strain | $OD_{660}$ | L-Gln (mg/L) |
|---|---|---|
| JGLE1/pSTV29 | 2.6 | 122.2 |
| JGLE1/pSnorM | 2.2 | 141.0 |
| JGLE1/pSrarD | 2.1 | 497.4 |

As shown in Table 2, an expression plasmid carrying the each of the norM gene (SEQ ID NO:1) or the rarD gene (SEQ ID NO:5) was introduced to increase the amount of expression of norM protein (SEQ ID NO:2) or rarD protein (SEQ ID NO:6), respectively; as a result, in both the cases, the amount of L-glutamine accumulated in the medium increased.

Example 4

Production of L-cysteine (L-Cys)

The *Escherichia coli* ATCC9637sdaABCcysE256 strain obtained in Preparation of Amino Acid Producers [4], which carries an expression plasmid for the cysE gene deregulated to L-cysteine, wherein L-serine degrading enzymes (sdaA, sdaB) and the uptake system (sdaC) were lacked, and the cysE gene on the chromosomal DNA was replaced by a deregulated cysE gene, was transformed with pScysEfbr1 obtained in Preparation of Amino Acid Producers [5] to acquire *Escherichia coli* ATCC9637sdaABCcysE256/pScysEfbr1, a microbial strain having the capability of producing L-cysteine biosynthesis intermediate (O-acetyl-L-serine) synthetase.

Next, *Escherichia coli* ATCC9637sdaABCcysE256/pScysEfbr was transformed with pSrarD, pSeamA and pSTV29 obtained in Example 1; the transformants obtained were named as *Escherichia coli* ATCC9637sdaABCcysE256/pScysEfbr1/pSrarD, *Escherichia coli* ATCC9637sdaABCcysE256/pScysEfbr1/pSeamA and *Escherichia coli* ATCC9637sdaABCcysE256/pScysEfbr1/pSTV29, respectively.

Each transformant obtained above was inoculated to a large test tube containing 5 ml of the same medium A as in Example 2 supplemented with 100 µg/ml ampicillin and 20 µg/ml chloramphenicol, and cultured at 30° C. for 16 hours.

The culture broth was inoculated at 10% to a test tube containing 5 ml of the medium D [the same composition as the medium B used in Example 2 except that glycine was not contained, and that 2 g/L thiosulfuric acid was contained] supplemented with 100 µg/ml ampicillin and 20 µg/ml chloramphenicol, and cultured at 30° C. for 24 hours, after which the culture broth was centrifuged, and a culture supernatant was acquired.

The products in the culture supernatant were analyzed using HPLC. The results are shown in Table 3.

TABLE 3

| E. coli strain | $OD_{660}$ | L-Cys (mg/L) |
|---|---|---|
| ATCC9637sdaABCcysE256/pScysEfbr1/pSTV29 | 63.0 | 73.4 |
| ATCC9637sdaABCcysE256/pScysEfbr1/pSrarD | 34.6 | 134.3 |
| ATCC9637sdaABCcysE256/pScysEfbr1/pSeamA | 21.0 | 355.6 |

As shown in Table 3, an expression plasmid carrying each of the rarD gene (SEQ ID NO:5) or the eamA gene (SEQ ID NO:7) was introduced to increase the amount expressed of rarD protein (SEQ ID NO:6) or eamA protein (SEQ ID NO:8), respectively; as a result, in both the cases, the amount of L-cysteine accumulated in the medium increased.

Example 5

Production of L-threonine (L-Thr)

The ATCC21277 strain [U.S. Pat. No. 3,580,810], an *Escherichia coli* strain that has been reported to produce L-threonine, was transformed with the pSeamA and pSTV29 obtained in Example 1; the transformants obtained were named as *Escherichia coli* ATCC21277/pSeamA and *Escherichia coli* ATCC21277/pSTV29, respectively.

Each transformant obtained above was inoculated to a large test tube containing 5 ml of the same medium A as in Example 2, supplemented with 20 µg/ml chloramphenicol, and cultured at 30° C. for 16 hours.

The culture broth was inoculated at 10% to a test tube containing 5 ml of the medium E [the same composition as the medium B used in Example 2 except that glycine and yeast extract were not contained, and that 5 g/L casamino acid was contained] supplemented with 20 µg/ml chloramphenicol, and cultured at 30° C. for 24 hours, after which the culture broth was centrifuged, and a culture supernatant was acquired.

The products in the culture supernatant were analyzed using HPLC. The results are shown in Table 4.

TABLE 4

| E. coil strain | $OD_{660}$ | L-Thr (mg/L) |
|---|---|---|
| ATCC21277/pSTV29 | 12.1 | 63.0 |
| ATCC21277/pSeamA | 7.5 | 110.6 |

As shown in Table 4, an expression plasmid carrying the norM gene (SEQ ID NO:1) was introduced to intensify the amount of expression of norM protein (SEQ ID NO:2); as a result, the amount of L-threonine accumulated in the medium increased.

Example 6

Production of L-phenylalanine (L-Phe)

The NM522 strain was transformed with the expression plasmid pBpheAfbraroFfbr wherein a deregulated aroF gene and a deregulated pheA gene were inserted in the forward orientation, prepared in [3] (2), to acquire *Escherichia coli* NM522/pBpheAfbraroFfbr, a transformant that produces L-phenylalanine synthetase.

Next, *Escherichia coli* NM522/pBpheAfbraroFfbr was transformed with pSemrD, pSrarD and pTV29 obtained in Example 1; the transformants obtained were named as *Escherichia coli* NM522/pBpheAfbraroFfbr/pSemrD, NM522/pBpheAfbraroFfbr/pSrarD and NM522/pBpheAfbraroFfbr/pSTV29, respectively.

Each transformant obtained above was inoculated to a large test tube containing 5 ml of the same medium A as in Example 2 supplemented with 100 μg/ml ampicillin and 20 μg/ml chloramphenicol, and cultured at 30° C. for 16 hours.

The culture broth was inoculated at 10% to a test tube containing 5 ml of the medium F [the same composition as the medium B used in Example 2 except that glycine was not contained] supplemented with 100 μg/ml ampicillin and 20 μg/ml chloramphenicol, and cultured at 30° C. for 24 hours, after which the culture broth was centrifuged, and a culture supernatant was acquired.

The products in the culture supernatant were analyzed using HPLC. The results are shown in Table 5.

TABLE 5

| *E. coli* strain | OD$_{660}$ | L-Phe (mg/L) |
|---|---|---|
| NM522/pBpheAfbraroFfbr/pSTV29 | 18.8 | 85.9 |
| NM522/pBpheAfbraroFfbr/pSemrD | 19.2 | 132.3 |
| NM522/pBpheAfbraroFfbr/pSrarD | 11.6 | 103.0 |

As shown in Table 5, an expression plasmid carrying each of the emrD gene (SEQ ID NO:3) or the rarD gene (SEQ ID NO:5) was introduced to increase the amount of expression of emerD protein (SEQ ID NO:4) or rarD protein (SEQ ID NO:6), respectively; as a result, in both the cases, the amount of L-phenylalanine accumulated in the medium increased.

Industrial Applicability

If a highly productive process for producing a L-amino acids is established to enable their industrial mass-production by the manufacturing process of the present invention, its industrial applicability would be very high. For example, L-serine is of high value for utilization as a raw material for amino acid mixtures in the field of pharmaceuticals and the field of cosmetics; L-glutamine serves as a raw material for anti-alcoholism compositions and the like. L-cysteine is an amino acid that is very highly valued in the cosmetic industry; L-threonine and L-phenylalanine are useful as an ingredient for amino acid infusions and health foods, and as a raw material for the low-calorie sweetener Aspartame, respectively.

This application is based on a patent application No. 2009-027881 filed in Japan (filing date: Feb. 9, 2009), the contents of which are incorporated in full herein.

[Sequence Listing Free Text]

SEQ ID NO:9—explanation of artificial sequence: synthetic DNA
SEQ ID NO:10—explanation of artificial sequence: synthetic DNA
SEQ ID NO:11—explanation of artificial sequence: synthetic DNA
SEQ ID NO:12—explanation of artificial sequence: synthetic DNA
SEQ ID NO:13—explanation of artificial sequence: synthetic DNA
SEQ ID NO:14—explanation of artificial sequence: synthetic DNA
SEQ ID NO:15—explanation of artificial sequence: synthetic DNA
SEQ ID NO:16—explanation of artificial sequence: synthetic DNA
SEQ ID NO:18—explanation of artificial sequence: synthetic DNA
SEQ ID NO:19—explanation of artificial sequence: synthetic DNA
SEQ ID NO:20—explanation of artificial sequence: synthetic DNA
SEQ ID NO:21—explanation of artificial sequence: synthetic DNA
SEQ ID NO:22—explanation of artificial sequence: synthetic DNA
SEQ ID NO:23—explanation of artificial sequence: synthetic DNA
SEQ ID NO:24—explanation of artificial sequence: synthetic DNA
SEQ ID NO:25—explanation of artificial sequence: synthetic DNA
SEQ ID NO:26—explanation of artificial sequence: synthetic DNA
SEQ ID NO:27—explanation of artificial sequence: synthetic DNA
SEQ ID NO:28—explanation of artificial sequence: synthetic DNA
SEQ ID NO:29—explanation of artificial sequence: synthetic DNA
SEQ ID NO:30—explanation of artificial sequence: synthetic DNA
SEQ ID NO:31—explanation of artificial sequence: synthetic DNA
SEQ ID NO:32—explanation of artificial sequence: synthetic DNA
SEQ ID NO:33—explanation of artificial sequence: synthetic DNA
SEQ ID NO:34—explanation of artificial sequence: synthetic DNA
SEQ ID NO:35—explanation of artificial sequence: synthetic DNA
SEQ ID NO:36—explanation of artificial sequence: synthetic DNA
SEQ ID NO:37—explanation of artificial sequence: synthetic DNA
SEQ ID NO:38—explanation of artificial sequence: synthetic DNA
SEQ ID NO:39—explanation of artificial sequence: synthetic DNA
SEQ ID NO:40—explanation of artificial sequence: synthetic DNA
SEQ ID NO:41—explanation of artificial sequence: synthetic DNA
SEQ ID NO:42—explanation of artificial sequence: synthetic DNA
SEQ ID NO:43—explanation of artificial sequence: synthetic DNA SEQ ID NO:44—explanation of artificial sequence: synthetic DNA
SEQ ID NO:45—explanation of artificial sequence: synthetic DNA
SEQ ID NO:46—explanation of artificial sequence: synthetic DNA
SEQ ID NO:47—explanation of artificial sequence: synthetic DNA

The invention claimed is:

1. A process for producing an L-amino acid which comprises:

(a) culturing, in a medium, a modified microorganism having L-amino acid transport activity and having a protein activity, wherein the protein is (1) a protein comprising the amino acid sequence of SEQ ID NO: 2, 4, or 6 or (2) a protein consisting of an amino acid sequence having 95% or more homology to the amino acid sequence of SEQ ID NO: 2, 4, or 6 and having L-amino acid transport activity, and wherein the protein activity is higher than that of the parent strain of the modified microorganism in the medium, (b) producing and accumulating the L-amino acid in the medium, and (c) collecting the L-amino acid from the medium.

2. The process of claim 1, wherein the modified microorganism is produced by (i) transformation of the parent strain with a DNA or (ii) modification in the parent strain of an expression regulatory sequence of the DNA, wherein the DNA is (1) a DNA that encodes (A) a protein comprising the amino acid sequence of SEQ ID NO: 2, 4, or 6 or (B) a protein consisting of an amino acid sequence having 95% or more homology to the amino acid sequence of SEQ ID NO: 2, 4, or 6 and having L-amino acid transport activity, (2) a DNA comprising the nucleotide sequence of SEQ ID NO: 1, 3, or 5, or (3) a DNA that hybridizes under stringent conditions with the DNA consisting of the nucleotide sequence complementary to the nucleotide sequence of SEQ ID NO: 1, 3, or 5 and encodes a protein having L-amino acid transport activity, wherein the stringent conditions are the conditions of incubating a DNA-immobilizing filter and a probe DNA in a solution containing 50% fonnamide, 5×SSC (750 mmol/L sodium chloride, 75 mmol/L sodium citrate), 50 mmol/L sodium phosphate (pH 7.6), 5×Denhardt's solution, 10% dextran sulfate, and 20 µg/L denatured salmon sperm DNA at 42° C. overnight, followed by washing the filter in a 0.2×SSC solution at about 65° C.

3. The process of claim 2, wherein the microorganism belongs to the genus *Escherichia*, the genus *Corynebacterium*, the genus *Bacillus*, the genus *Serratia*, the genus *Pseudomonas* or the genus *Streptomyces*.

4. The process of claim 3, wherein the L-amino acid is selected from the group consisting of L-serine, L-glutamine, L-cysteine, L-phenylalanine and L-threonine.

5. The process of claim 1, wherein the microorganism belongs to the genus *Escherichia*, the genus *Corynebacterium*, the genus *Bacillus*, the genus *Serratia*, the genus *Pseudomonas* or the genus *Streptomyces*.

6. The process of claim 5, wherein the L-amino acid is selected from the group consisting of L-serine, L-glutamine, L-cysteine, L-phenylalanine and L-threonine.

7. The process of claim 2, wherein the L-amino acid is selected from the group consisting of L-serine, L-glutamine, L-cysteine, L-phenylalanine and L-threonine.

8. The process of claim 1, wherein the L-amino acid is selected from the group consisting of L-serine, L-glutamine, L-cysteine, L-phenylalanine and L-threonine.

9. The process of claim 1, wherein the protein comprises the amino acid sequence of SEQ ID NO: 2, 4, or 6.

10. The process of claim 1, wherein the protein consists of an amino acid sequence having 95% or more homology to the amino acid sequence of SEQ ID NO: 2, 4, or 6 and having L-amino acid transport activity.

11. The process of claim 2, wherein the DNA encodes a protein comprising the amino acid sequence of SEQ ID NO: 2, 4, or 6.

12. The process of claim 2, wherein the DNA encodes a protein consisting of an amino acid sequence having 95% or more homology to the amino acid sequence of SEQ ID NO: 2, 4, or 6 and having L-amino acid transport activity.

13. The process of claim 2, wherein the DNA comprises the nucleotide sequence of SEQ ID NO: 1, 3, or 5.

14. The process of claim 2, wherein the DNA that hybridizes under stringent conditions with the DNA consisting of the nucleotide sequence complementary to the nucleotide sequence of SEQ ID NO: 1, 3, or 5, and encodes a protein having L-amino acid transport activity, wherein the stringent conditions are the conditions of incubating a DNA-immobilizing filter and a probe DNA in a solution containing 50% formamide, 5×SSC (750 mmol/L sodium chloride, 75 mmol/L sodium citrate), 50 mmol/L sodium phosphate (pH 7.6), 5×Denhardt's solution, 10% dextran sulfate, and 20 µg/L denatured salmon sperm DNA at 42° C. overnight, followed by washing the filter in a 0.2×SSC solution at about 65° C.

\* \* \* \* \*

```
                        SEQUENCE LISTING

<160> NUMBER OF SEQ ID NOS: 47

<210> SEQ ID NO 1
<211> LENGTH: 1374
<212> TYPE: DNA
<213> ORGANISM: Escherichia coli
<220> FEATURE:
<221> NAME/KEY: CDS
<222> LOCATION: (1)..(1374)

<400> SEQUENCE: 1 gtg cag aag tat atc agt gaa gcg cgt ctg tta tta gca tta gca atc      48
Met Gln Lys Tyr Ile Ser Glu Ala Arg Leu Leu Leu Ala Leu Ala Ile
1               5                  10                  15 ccg gtg att ctc gcg caa atc gcc caa act gcg atg ggt ttt gtc agt      96
Pro Val Ile Leu Ala Gln Ile Ala Gln Thr Ala Met Gly Phe Val Ser
            20                  25                  30 acc gtg atg gcg ggc ggc tat agt gcc acc gac atg gcg gcg gtc gct     144
Thr Val Met Ala Gly Gly Tyr Ser Ala Thr Asp Met Ala Ala Val Ala
        35                  40                  45 atc ggt act tct atc tgg ctt ccg gcg atc ctc ttt ggt cac gga ctg     192
Ile Gly Thr Ser Ile Trp Leu Pro Ala Ile Leu Phe Gly His Gly Leu
    50                  55                  60 ctg ctg gca tta acg ccg gtt atc gcg caa tta aat ggt tcc ggt cga     240
Leu Leu Ala Leu Thr Pro Val Ile Ala Gln Leu Asn Gly Ser Gly Arg
65                  70                  75                  80 cgt gag cgc att gcg cat cag gtg cga caa ggt ttc tgg ctg gca ggt     288
Arg Glu Arg Ile Ala His Gln Val Arg Gln Gly Phe Trp Leu Ala Gly
                85                  90                  95 ttt gtt tcc gtt ctc att atg ctg gtg ctg tgg aat gca ggt tac att     336
Phe Val Ser Val Leu Ile Met Leu Val Leu Trp Asn Ala Gly Tyr Ile
            100                 105                 110 atc cgc tcc atg gaa aac atc gat ccg gct ctg gcg gac aaa gcc gtg     384
Ile Arg Ser Met Glu Asn Ile Asp Pro Ala Leu Ala Asp Lys Ala Val
        115                 120                 125 ggt tat ctg cgt gcg ttg ttg tgg ggc gcg ccg gga tat ctg ttc ttc     432
Gly Tyr Leu Arg Ala Leu Leu Trp Gly Ala Pro Gly Tyr Leu Phe Phe
    130                 135                 140 cag gtt gcc cgt aac cag tgt gaa ggt ctg gca aaa acc aag ccg ggt     480
Gln Val Ala Arg Asn Gln Cys Glu Gly Leu Ala Lys Thr Lys Pro Gly
145                 150                 155                 160 atg gta atg ggc ttt atc ggc ctg ctg gtg aac atc ccg gtg aac tat     528
Met Val Met Gly Phe Ile Gly Leu Leu Val Asn Ile Pro Val Asn Tyr
                165                 170                 175 atc ttt att tat ggt cat ttc ggt atg cct gag ctc ggt ggc gtt ggt     576
Ile Phe Ile Tyr Gly His Phe Gly Met Pro Glu Leu Gly Gly Val Gly
            180                 185                 190 tgt ggc gtg gct act gcg gcg gtg tat tgg gtc atg ttc ctt gcc atg     624
Cys Gly Val Ala Thr Ala Ala Val Tyr Trp Val Met Phe Leu Ala Met
        195                 200                 205 gtt tct tac att aaa cgc gcc cgc tcc atg cgc gat att cgt aac gaa     672
Val Ser Tyr Ile Lys Arg Ala Arg Ser Met Arg Asp Ile Arg Asn Glu
    210                 215                 220 aaa ggc acc gca aaa ccc gat cct gcg gtt atg aaa cga ctg att caa     720
Lys Gly Thr Ala Lys Pro Asp Pro Ala Val Met Lys Arg Leu Ile Gln
225                 230                 235                 240
```

| | | | | | | | | | | | | | | | |
|---|---|---|---|---|---|---|---|---|---|---|---|---|---|---|---|
| ctc | ggt | ttg | ccg | att | gcg | ctg | gca | ctg | ttc | ttt | gaa | gtg | aca | ctg | ttt | 768
| Leu | Gly | Leu | Pro | Ile | Ala | Leu | Ala | Leu | Phe | Phe | Glu | Val | Thr | Leu | Phe |
| | | | 245 | | | | | 250 | | | | | 255 | | |
| gcc | gtc | gtg | gct | ctg | tta | gtg | tct | ccg | ctc | ggt | att | gtt | gat | gtc | gca | 816
| Ala | Val | Val | Ala | Leu | Leu | Val | Ser | Pro | Leu | Gly | Ile | Val | Asp | Val | Ala |
| | | 260 | | | | | 265 | | | | | 270 | | | |
| gga | cac | cag | att | gcc | ctg | aac | ttt | agt | tca | cta | atg | ttc | gtg | ctt | cca | 864
| Gly | His | Gln | Ile | Ala | Leu | Asn | Phe | Ser | Ser | Leu | Met | Phe | Val | Leu | Pro |
| | | 275 | | | | | 280 | | | | | 285 | | | |
| atg | tcg | ctg | gcg | gca | gcg | gta | act | atc | cgc | gta | ggt | tat | cgt | ctg | ggt | 912
| Met | Ser | Leu | Ala | Ala | Ala | Val | Thr | Ile | Arg | Val | Gly | Tyr | Arg | Leu | Gly |
| | | 290 | | | | | 295 | | | | | 300 | | | |
| cag | ggc | tca | acg | ctg | gat | gcg | caa | acc | gct | gcg | cgg | acc | ggg | ctt | atg | 960
| Gln | Gly | Ser | Thr | Leu | Asp | Ala | Gln | Thr | Ala | Ala | Arg | Thr | Gly | Leu | Met |
| 305 | | | | 310 | | | | | 315 | | | | | 320 | |
| gtg | ggt | gtc | tgt | atg | gca | acc | ctg | acg | gcc | att | ttc | acg | gtt | tca | ctg | 1008
| Val | Gly | Val | Cys | Met | Ala | Thr | Leu | Thr | Ala | Ile | Phe | Thr | Val | Ser | Leu |
| | | | 325 | | | | | 330 | | | | | 335 | | |
| cgg | gag | caa | atc | gcc | ctg | ttg | tac | aac | gac | aat | ccc | gag | gtt | gta | acg | 1056
| Arg | Glu | Gln | Ile | Ala | Leu | Leu | Tyr | Asn | Asp | Asn | Pro | Glu | Val | Val | Thr |
| | | | 340 | | | | | 345 | | | | | 350 | | |
| ctg | gct | gcg | cat | ttg | atg | ttg | ctg | gcg | gcg | gta | tat | cag | att | tct | gac | 1104
| Leu | Ala | Ala | His | Leu | Met | Leu | Leu | Ala | Ala | Val | Tyr | Gln | Ile | Ser | Asp |
| | | | 355 | | | | | 360 | | | | | 365 | | |
| tca | atc | cag | gtg | att | ggc | agt | ggg | att | ttg | cgt | ggt | tat | aaa | gat | acg | 1152
| Ser | Ile | Gln | Val | Ile | Gly | Ser | Gly | Ile | Leu | Arg | Gly | Tyr | Lys | Asp | Thr |
| | 370 | | | | | 375 | | | | | 380 | | | | |
| cgt | tcc | att | ttc | tat | att | acc | ttt | acg | gct | tac | tgg | gtg | ctg | ggc | ttg | 1200
| Arg | Ser | Ile | Phe | Tyr | Ile | Thr | Phe | Thr | Ala | Tyr | Trp | Val | Leu | Gly | Leu |
| 385 | | | | | 390 | | | | | 395 | | | | | 400 |
| cca | agc | ggc | tat | att | ctg | gca | ctg | acc | gat | ctg | gtc | gtt | gaa | cct | atg | 1248
| Pro | Ser | Gly | Tyr | Ile | Leu | Ala | Leu | Thr | Asp | Leu | Val | Val | Glu | Pro | Met |
| | | | 405 | | | | | 410 | | | | | 415 | | |
| ggg | cca | gca | ggc | ttc | tgg | ata | ggc | ttt | att | att | ggc | ctg | acg | tcg | gca | 1296
| Gly | Pro | Ala | Gly | Phe | Trp | Ile | Gly | Phe | Ile | Ile | Gly | Leu | Thr | Ser | Ala |
| | | | 420 | | | | | 425 | | | | | 430 | | |
| gcc | att | atg | atg | atg | ttg | cgt | atg | cgg | ttc | ctg | caa | cgt | ctg | ccg | tca | 1344
| Ala | Ile | Met | Met | Met | Leu | Arg | Met | Arg | Phe | Leu | Gln | Arg | Leu | Pro | Ser |
| | | | 435 | | | | | 440 | | | | | 445 | | |
| gcc | atc | att | ctg | caa | cga | gca | tcc | cgc | taa | | | | | | | 1374
| Ala | Ile | Ile | Leu | Gln | Arg | Ala | Ser | Arg | | | | | | | |
| | | 450 | | | | | 455 | | | | | | | | |

<210> SEQ ID NO 2
<211> LENGTH: 457
<212> TYPE: PRT
<213> ORGANISM: Escherichia coli

<400> SEQUENCE: 2

Met Gln Lys Tyr Ile Ser Glu Ala Arg Leu Leu Leu Ala Leu Ala Ile
1               5                   10                  15

Pro Val Ile Leu Ala Gln Ile Ala Gln Thr Ala Met Gly Phe Val Ser
                20                  25                  30

Thr Val Met Ala Gly Gly Tyr Ser Ala Thr Asp Met Ala Ala Val Ala
            35                  40                  45

Ile Gly Thr Ser Ile Trp Leu Pro Ala Ile Leu Phe Gly His Gly Leu
        50                  55                  60

Leu Leu Ala Leu Thr Pro Val Ile Ala Gln Leu Asn Gly Ser Gly Arg
65                  70                  75                  80

```
Arg Glu Arg Ile Ala His Gln Val Arg Gln Gly Phe Trp Leu Ala Gly
                    85                  90                  95

Phe Val Ser Val Leu Ile Met Leu Val Leu Trp Asn Ala Gly Tyr Ile
            100                 105                 110

Ile Arg Ser Met Glu Asn Ile Asp Pro Ala Leu Ala Asp Lys Ala Val
            115                 120                 125

Gly Tyr Leu Arg Ala Leu Leu Trp Gly Ala Pro Gly Tyr Leu Phe Phe
        130                 135                 140

Gln Val Ala Arg Asn Gln Cys Glu Gly Leu Ala Lys Thr Lys Pro Gly
145                 150                 155                 160

Met Val Met Gly Phe Ile Gly Leu Leu Val Asn Ile Pro Val Asn Tyr
                165                 170                 175

Ile Phe Ile Tyr Gly His Phe Gly Met Pro Glu Leu Gly Gly Val Gly
            180                 185                 190

Cys Gly Val Ala Thr Ala Val Tyr Trp Val Met Phe Leu Ala Met
        195                 200                 205

Val Ser Tyr Ile Lys Arg Ala Arg Ser Met Arg Asp Ile Arg Asn Glu
        210                 215                 220

Lys Gly Thr Ala Lys Pro Asp Pro Ala Val Met Lys Arg Leu Ile Gln
225                 230                 235                 240

Leu Gly Leu Pro Ile Ala Leu Ala Leu Phe Phe Glu Val Thr Leu Phe
                245                 250                 255

Ala Val Val Ala Leu Leu Val Ser Pro Leu Gly Ile Val Asp Val Ala
            260                 265                 270

Gly His Gln Ile Ala Leu Asn Phe Ser Ser Leu Met Phe Val Leu Pro
        275                 280                 285

Met Ser Leu Ala Ala Ala Val Thr Ile Arg Val Gly Tyr Arg Leu Gly
290                 295                 300

Gln Gly Ser Thr Leu Asp Ala Gln Thr Ala Ala Arg Thr Gly Leu Met
305                 310                 315                 320

Val Gly Val Cys Met Ala Thr Leu Thr Ala Ile Phe Thr Val Ser Leu
                325                 330                 335

Arg Glu Gln Ile Ala Leu Leu Tyr Asn Asp Asn Pro Glu Val Val Thr
            340                 345                 350

Leu Ala Ala His Leu Met Leu Leu Ala Ala Val Tyr Gln Ile Ser Asp
        355                 360                 365

Ser Ile Gln Val Ile Gly Ser Gly Ile Leu Arg Gly Tyr Lys Asp Thr
370                 375                 380

Arg Ser Ile Phe Tyr Ile Thr Phe Thr Ala Tyr Trp Val Leu Gly Leu
385                 390                 395                 400

Pro Ser Gly Tyr Ile Leu Ala Leu Thr Asp Leu Val Val Glu Pro Met
                405                 410                 415

Gly Pro Ala Gly Phe Trp Ile Gly Phe Ile Ile Gly Leu Thr Ser Ala
            420                 425                 430

Ala Ile Met Met Met Leu Arg Met Arg Phe Leu Gln Arg Leu Pro Ser
        435                 440                 445

Ala Ile Ile Leu Gln Arg Ala Ser Arg
        450                 455

<210> SEQ ID NO 3
<211> LENGTH: 1185
<212> TYPE: DNA
<213> ORGANISM: Escherichia coli
<220> FEATURE:
<221> NAME/KEY: CDS
<222> LOCATION: (1)..(1185)
```

<400> SEQUENCE: 3

```
atg aaa agg caa aga aac gtc aat ttg tta ttg atg ttg gta tta ctc      48
Met Lys Arg Gln Arg Asn Val Asn Leu Leu Leu Met Leu Val Leu Leu
1               5                   10                  15 gtg gcc gtc ggt cag atg gcg caa acc att tat att cca gct att gcc      96
Val Ala Val Gly Gln Met Ala Gln Thr Ile Tyr Ile Pro Ala Ile Ala
            20                  25                  30 gat atg gcg cgc gat ctc aac gtc cgt gaa ggg gcg gtg cag agc gta     144
Asp Met Ala Arg Asp Leu Asn Val Arg Glu Gly Ala Val Gln Ser Val
        35                  40                  45 atg ggc gct tat ctg ctg act tac ggt gtc tca cag ctg ttt tat ggc     192
Met Gly Ala Tyr Leu Leu Thr Tyr Gly Val Ser Gln Leu Phe Tyr Gly
    50                  55                  60 ccg att tcc gac cgc gtg ggc cgc cga ccg gtg atc ctc gtc gga atg     240
Pro Ile Ser Asp Arg Val Gly Arg Arg Pro Val Ile Leu Val Gly Met
65                  70                  75                  80 tcc att ttt atg ctg gca acg ctg gtc gcg gtc acg acc tcc agt ttg     288
Ser Ile Phe Met Leu Ala Thr Leu Val Ala Val Thr Thr Ser Ser Leu
                85                  90                  95 acg gtg ttg att gcc gcc agc gcg atg cag ggg atg ggc acc ggc gtt     336
Thr Val Leu Ile Ala Ala Ser Ala Met Gln Gly Met Gly Thr Gly Val
            100                 105                 110 ggc ggc gta atg gcg cgt act tta ccg cga gat tta tat gaa cgg aca     384
Gly Gly Val Met Ala Arg Thr Leu Pro Arg Asp Leu Tyr Glu Arg Thr
        115                 120                 125 cag ttg cgc cat gct aac agc ctg tta aac atg ggg att ctc gtc agt     432
Gln Leu Arg His Ala Asn Ser Leu Leu Asn Met Gly Ile Leu Val Ser
    130                 135                 140 ccg ttg ctc gca ccg cta atc ggc ggt ctg ctg gat acg atg tgg aac     480
Pro Leu Leu Ala Pro Leu Ile Gly Gly Leu Leu Asp Thr Met Trp Asn
145                 150                 155                 160 tgg cgc gcc tgt tat ctc ttt ttg ttg gtt ctt tgt gct ggt gtg acc     528
Trp Arg Ala Cys Tyr Leu Phe Leu Leu Val Leu Cys Ala Gly Val Thr
                165                 170                 175 ttc agt atg gcc cgc tgg atg ccg gaa acg cgt ccg gtc gat gca ccg     576
Phe Ser Met Ala Arg Trp Met Pro Glu Thr Arg Pro Val Asp Ala Pro
            180                 185                 190 cgc acg cgc ctg ctt acc agt tat aaa acg ctt ttc ggt aac agc ggt     624
Arg Thr Arg Leu Leu Thr Ser Tyr Lys Thr Leu Phe Gly Asn Ser Gly
        195                 200                 205 ttt aac tgt tat ttg ctg atg ctg att ggc ggt ctg gcc ggg att gcc     672
Phe Asn Cys Tyr Leu Leu Met Leu Ile Gly Gly Leu Ala Gly Ile Ala
    210                 215                 220 gcc ttt gaa gcc tgc tcc ggc gtg ctg atg ggc gcg gtg tta ggg ctg     720
Ala Phe Glu Ala Cys Ser Gly Val Leu Met Gly Ala Val Leu Gly Leu
225                 230                 235                 240 agc agt atg acg gtc agt att ttg ttt att ctg ccg att ccg gca gcg     768
Ser Ser Met Thr Val Ser Ile Leu Phe Ile Leu Pro Ile Pro Ala Ala
                245                 250                 255 ttt ttt ggc gca tgg ttt gcc gga cgt ccc aat aaa cgc ttc tcc acg     816
Phe Phe Gly Ala Trp Phe Ala Gly Arg Pro Asn Lys Arg Phe Ser Thr
            260                 265                 270 tta atg tgg cag tcg gtt atc tgc tgc ctg ctg gct ggc ttg ctg atg     864
Leu Met Trp Gln Ser Val Ile Cys Cys Leu Leu Ala Gly Leu Leu Met
        275                 280                 285 tgg atc ccc gac tgg ttt ggc gtg atg aat gtc tgg acg ctc ctc gtt     912
Trp Ile Pro Asp Trp Phe Gly Val Met Asn Val Trp Thr Leu Leu Val
    290                 295                 300 ccc gcc gcg ctg ttc ttt ttc ggt gcc ggg atg ctg ttt ccg ctg gcg     960
Pro Ala Ala Leu Phe Phe Phe Gly Ala Gly Met Leu Phe Pro Leu Ala
```

```
Pro Ala Ala Leu Phe Phe Phe Gly Ala Gly Met Leu Phe Pro Leu Ala
305                 310                 315                 320 acc agc ggc gcg atg gag ccg ttc ccc ttc ctg gcg ggc acg gct ggc      1008
Thr Ser Gly Ala Met Glu Pro Phe Pro Phe Leu Ala Gly Thr Ala Gly
                325                 330                 335 gcg ctg gtc ggc ggt ctg caa aac att ggt tcc ggc gtg ctg gcg tcg      1056
Ala Leu Val Gly Gly Leu Gln Asn Ile Gly Ser Gly Val Leu Ala Ser
            340                 345                 350 ctc tct gcg atg ttg ccg caa acc ggt cag ggc agc ctg ggg ttg ttg      1104
Leu Ser Ala Met Leu Pro Gln Thr Gly Gln Gly Ser Leu Gly Leu Leu
        355                 360                 365 atg acc tta atg gga ttg ttg atc gtg ctg tgc tgg ctg ccg ctg gcg      1152
Met Thr Leu Met Gly Leu Leu Ile Val Leu Cys Trp Leu Pro Leu Ala
    370                 375                 380 acg cgg atg tcg cat cag ggg cag ccc gtt taa                          1185
Thr Arg Met Ser His Gln Gly Gln Pro Val
385                 390
```

<210> SEQ ID NO 4
<211> LENGTH: 394
<212> TYPE: PRT
<213> ORGANISM: Escherichia coli

<400> SEQUENCE: 4

```
Met Lys Arg Gln Arg Asn Val Asn Leu Leu Met Leu Val Leu Leu
1               5                   10                  15

Val Ala Val Gly Gln Met Ala Gln Thr Ile Tyr Ile Pro Ala Ile
            20                  25                  30

Asp Met Ala Arg Asp Leu Asn Val Arg Glu Gly Ala Val Gln Ser Val
        35                  40                  45

Met Gly Ala Tyr Leu Leu Thr Tyr Gly Val Ser Gln Leu Phe Tyr Gly
    50                  55                  60

Pro Ile Ser Asp Arg Val Gly Arg Arg Pro Val Ile Leu Val Gly Met
65                  70                  75                  80

Ser Ile Phe Met Leu Ala Thr Leu Val Ala Val Thr Thr Ser Ser Leu
                85                  90                  95

Thr Val Leu Ile Ala Ala Ser Ala Met Gln Gly Met Gly Thr Gly Val
            100                 105                 110

Gly Gly Val Met Ala Arg Thr Leu Pro Arg Asp Leu Tyr Glu Arg Thr
        115                 120                 125

Gln Leu Arg His Ala Asn Ser Leu Leu Asn Met Gly Ile Leu Val Ser
    130                 135                 140

Pro Leu Leu Ala Pro Leu Ile Gly Gly Leu Leu Asp Thr Met Trp Asn
145                 150                 155                 160

Trp Arg Ala Cys Tyr Leu Phe Leu Leu Val Leu Cys Ala Gly Val Thr
                165                 170                 175

Phe Ser Met Ala Arg Trp Met Pro Glu Thr Arg Pro Val Asp Ala Pro
            180                 185                 190

Arg Thr Arg Leu Leu Thr Ser Tyr Lys Thr Leu Phe Gly Asn Ser Gly
        195                 200                 205

Phe Asn Cys Tyr Leu Leu Met Leu Ile Gly Gly Leu Ala Gly Ile Ala
    210                 215                 220

Ala Phe Glu Ala Cys Ser Gly Val Leu Met Gly Ala Val Leu Gly Leu
225                 230                 235                 240

Ser Ser Met Thr Val Ser Ile Leu Phe Ile Leu Pro Ile Pro Ala Ala
                245                 250                 255

Phe Phe Gly Ala Trp Phe Ala Gly Arg Pro Asn Lys Arg Phe Ser Thr
```

-continued

```
                       260                 265                 270
Leu Met Trp Gln Ser Val Ile Cys Cys Leu Leu Ala Gly Leu Leu Met
            275                 280                 285

Trp Ile Pro Asp Trp Phe Gly Val Met Asn Val Trp Thr Leu Leu Val
        290                 295                 300

Pro Ala Leu Phe Phe Phe Gly Ala Gly Met Leu Phe Pro Leu Ala
305                 310                 315                 320

Thr Ser Gly Ala Met Glu Pro Phe Pro Phe Leu Ala Gly Thr Ala Gly
                    325                 330                 335

Ala Leu Val Gly Gly Leu Gln Asn Ile Gly Ser Gly Val Leu Ala Ser
                340                 345                 350

Leu Ser Ala Met Leu Pro Gln Thr Gly Gln Gly Ser Leu Gly Leu Leu
            355                 360                 365

Met Thr Leu Met Gly Leu Leu Ile Val Leu Cys Trp Leu Pro Leu Ala
        370                 375                 380

Thr Arg Met Ser His Gln Gly Gln Pro Val
385                 390

<210> SEQ ID NO 5
<211> LENGTH: 891
<212> TYPE: DNA
<213> ORGANISM: Escherichia coli
<220> FEATURE:
<221> NAME/KEY: CDS
<222> LOCATION: (1)..(891)

<400> SEQUENCE: 5 atg gat gca aaa caa acg cgg cag ggc gta tta ctc gct ctt gcc gct    48
Met Asp Ala Lys Gln Thr Arg Gln Gly Val Leu Leu Ala Leu Ala Ala
1               5                   10                  15 tat ttt att tgg ggt ata gcg cca gcg tac ttc aag ttg att tac tac    96
Tyr Phe Ile Trp Gly Ile Ala Pro Ala Tyr Phe Lys Leu Ile Tyr Tyr
            20                  25                  30 gtg ccc gcc gat gaa atc ctg acg cat cgc gtg atc tgg tcg ttt ttc   144
Val Pro Ala Asp Glu Ile Leu Thr His Arg Val Ile Trp Ser Phe Phe
        35                  40                  45 ttt atg gtg gtg ctg atg agc att tgc gcg cag tgg tcc tat tta aaa   192
Phe Met Val Val Leu Met Ser Ile Cys Arg Gln Trp Ser Tyr Leu Lys
    50                  55                  60 acg ctg att cag acg cca cag aaa att ttt atg ctg gca gtc tct gcc   240
Thr Leu Ile Gln Thr Pro Gln Lys Ile Phe Met Leu Ala Val Ser Ala
65                  70                  75                  80 gtg ctg att ggt ggc aac tgg cta ctg ttt atc tgg gcg gtg aac aat   288
Val Leu Ile Gly Gly Asn Trp Leu Leu Phe Ile Trp Ala Val Asn Asn
                85                  90                  95 cac cat atg ctg gaa gcg agc ctt ggt tac ttt att aac ccg ctg gtg   336
His His Met Leu Glu Ala Ser Leu Gly Tyr Phe Ile Asn Pro Leu Val
            100                 105                 110 aac att gtg ctg ggg atg att ttc ctc ggc gag cga ttc cgc gga atg   384
Asn Ile Val Leu Gly Met Ile Phe Leu Gly Glu Arg Phe Arg Arg Met
        115                 120                 125 caa tgg ctg gcg gtg att ctg gcg ata tgt ggc gtg tta gtc cag ctg   432
Gln Trp Leu Ala Val Ile Leu Ala Ile Cys Gly Val Leu Val Gln Leu
    130                 135                 140 tgg act ttt ggt tcg cta cct att atc gcg ctg gga ctg gca ttt agt   480
Trp Thr Phe Gly Ser Leu Pro Ile Ile Ala Leu Gly Leu Ala Phe Ser
145                 150                 155                 160 ttt gcc ttc tac ggt ctg gta cgc aag aag att gcc gtt gaa gcg caa   528
Phe Ala Phe Tyr Gly Leu Val Arg Lys Lys Ile Ala Val Glu Ala Gln
                165                 170                 175
```

-continued

```
acc ggc atg tta atc gaa acc atg tgg ctg ctg ccc gtg gcg gca att    576
Thr Gly Met Leu Ile Glu Thr Met Trp Leu Leu Pro Val Ala Ala Ile
        180                 185                 190 tac ctg ttt gct att gcc gac agc tca acc agc cat atg ggg caa aac    624
Tyr Leu Phe Ala Ile Ala Asp Ser Ser Thr Ser His Met Gly Gln Asn
            195                 200                 205 ccg atg tcg ctg aat tta ctg ctg atc gcc gcc ggt att gtc act acc    672
Pro Met Ser Leu Asn Leu Leu Leu Ile Ala Ala Gly Ile Val Thr Thr
    210                 215                 220 gta ccg ctg ttg tgt ttt acc gcc gct gcc acg cgc ttg cgt ctc tca    720
Val Pro Leu Leu Cys Phe Thr Ala Ala Ala Thr Arg Leu Arg Leu Ser
225                 230                 235                 240 acg tta ggc ttt ttc cag tac att ggc ccg acg ctg atg ttc ctg ctg    768
Thr Leu Gly Phe Phe Gln Tyr Ile Gly Pro Thr Leu Met Phe Leu Leu
                245                 250                 255 gct gtg acg ttt tat ggt gaa aaa ccg ggt gcc gat aag atg gtg act    816
Ala Val Thr Phe Tyr Gly Glu Lys Pro Gly Ala Asp Lys Met Val Thr
            260                 265                 270 ttc gcc ttt att tgg gtg gcg ctg gca att ttt gtg atg gat gcg att    864
Phe Ala Phe Ile Trp Val Ala Leu Ala Ile Phe Val Met Asp Ala Ile
        275                 280                 285 tat acg cag cgt aga acg tcc aaa taa                                891
Tyr Thr Gln Arg Arg Thr Ser Lys
290                 295

<210> SEQ ID NO 6
<211> LENGTH: 296
<212> TYPE: PRT
<213> ORGANISM: Escherichia coli

<400> SEQUENCE: 6

Met Asp Ala Lys Gln Thr Arg Gln Gly Val Leu Leu Ala Leu Ala Ala
1               5                   10                  15

Tyr Phe Ile Trp Gly Ile Ala Pro Ala Tyr Phe Lys Leu Ile Tyr Tyr
                20                  25                  30

Val Pro Ala Asp Glu Ile Leu Thr His Arg Val Ile Trp Ser Phe Phe
            35                  40                  45

Phe Met Val Val Leu Met Ser Ile Cys Arg Gln Trp Ser Tyr Leu Lys
        50                  55                  60

Thr Leu Ile Gln Thr Pro Gln Lys Ile Phe Met Leu Ala Val Ser Ala
65                  70                  75                  80

Val Leu Ile Gly Gly Asn Trp Leu Leu Phe Ile Trp Ala Val Asn Asn
                85                  90                  95

His His Met Leu Glu Ala Ser Leu Gly Tyr Phe Ile Asn Pro Leu Val
            100                 105                 110

Asn Ile Val Leu Gly Met Ile Phe Leu Gly Glu Arg Phe Arg Arg Met
        115                 120                 125

Gln Trp Leu Ala Val Ile Leu Ala Ile Cys Gly Val Leu Val Gln Leu
    130                 135                 140

Trp Thr Phe Gly Ser Leu Pro Ile Ile Ala Leu Gly Leu Ala Phe Ser
145                 150                 155                 160

Phe Ala Phe Tyr Gly Leu Val Arg Lys Lys Ile Ala Val Glu Ala Gln
                165                 170                 175

Thr Gly Met Leu Ile Glu Thr Met Trp Leu Leu Pro Val Ala Ala Ile
            180                 185                 190

Tyr Leu Phe Ala Ile Ala Asp Ser Ser Thr Ser His Met Gly Gln Asn
        195                 200                 205
```

```
Pro Met Ser Leu Asn Leu Leu Leu Ile Ala Ala Gly Ile Val Thr Thr
    210                 215                 220

Val Pro Leu Leu Cys Phe Thr Ala Ala Ala Thr Arg Leu Arg Leu Ser
225                 230                 235                 240

Thr Leu Gly Phe Phe Gln Tyr Ile Gly Pro Thr Leu Met Phe Leu Leu
                245                 250                 255

Ala Val Thr Phe Tyr Gly Glu Lys Pro Gly Ala Asp Lys Met Val Thr
                260                 265                 270

Phe Ala Phe Ile Trp Val Ala Leu Ala Ile Phe Val Met Asp Ala Ile
            275                 280                 285

Tyr Thr Gln Arg Arg Thr Ser Lys
    290                 295

<210> SEQ ID NO 7
<211> LENGTH: 900
<212> TYPE: DNA
<213> ORGANISM: Escherichia coli
<220> FEATURE:
<221> NAME/KEY: CDS
<222> LOCATION: (1)..(900)

<400> SEQUENCE: 7 atg tcg cga aaa gat ggg gtg ttg gcg cta ctg gta gtg gtc gta tgg      48
Met Ser Arg Lys Asp Gly Val Leu Ala Leu Leu Val Val Val Val Trp
1               5                   10                  15 ggg cta aat ttt gtg gtc atc aaa gtg ggg ctt cat aac atg cca ccg      96
Gly Leu Asn Phe Val Val Ile Lys Val Gly Leu His Asn Met Pro Pro
                20                  25                  30 ctg atg ctg gcc ggt ttg cgc ttt atg ctg gtc gct ttt ccg gct atc     144
Leu Met Leu Ala Gly Leu Arg Phe Met Leu Val Ala Phe Pro Ala Ile
            35                  40                  45 ttt ttt gtc gca cga ccg aaa gta cca ctg aat ttg ctg ctg ggg tat     192
Phe Phe Val Ala Arg Pro Lys Val Pro Leu Asn Leu Leu Leu Gly Tyr
        50                  55                  60 gga tta acc atc agt ttt gcg cag ttt gct ttt ctt ttt tgt gcc att     240
Gly Leu Thr Ile Ser Phe Ala Gln Phe Ala Phe Leu Phe Cys Ala Ile
65                  70                  75                  80 aac ttc ggt atg cct gct gga ctg gct tcg ctg gtg tta cag gca cag     288
Asn Phe Gly Met Pro Ala Gly Leu Ala Ser Leu Val Leu Gln Ala Gln
                85                  90                  95 gcg ttt ttt act atc atg ctt ggc gcg ttt act ttc ggg gag cga ctg     336
Ala Phe Phe Thr Ile Met Leu Gly Ala Phe Thr Phe Gly Glu Arg Leu
            100                 105                 110 cat ggc aaa caa ttg gcg ggg atc gcc tta gcg att ttt ggc gta ctg     384
His Gly Lys Gln Leu Ala Gly Ile Ala Leu Ala Ile Phe Gly Val Leu
        115                 120                 125 gtg tta atc gaa gat agt ctg aac ggt cag cat gtg gcg atg ctc ggc     432
Val Leu Ile Glu Asp Ser Leu Asn Gly Gln His Val Ala Met Leu Gly
    130                 135                 140 ttt atg ttg acc ctg gcg gca gca ttt agt tgg gcg tgt ggc aac atc     480
Phe Met Leu Thr Leu Ala Ala Ala Phe Ser Trp Ala Cys Gly Asn Ile
145                 150                 155                 160 ttc aat aaa aag atc atg tcg cac tca acg cgt ccg gcg gtg atg tcg     528
Phe Asn Lys Lys Ile Met Ser His Ser Thr Arg Pro Ala Val Met Ser
                165                 170                 175 ctg gta atc tgg agc gct tta atc cca atc att ccc ttc ttt gtt gcc     576
Leu Val Ile Trp Ser Ala Leu Ile Pro Ile Ile Pro Phe Phe Val Ala
            180                 185                 190 tcg ctg att ctc gat ggt tcc gca acc atg att cac agt ctg gtt act     624
Ser Leu Ile Leu Asp Gly Ser Ala Thr Met Ile His Ser Leu Val Thr
        195                 200                 205
```

-continued

```
atc gat atg acc acc atc ttg tct ctg atg tat ctg gcg ttt gtg gcg      672
Ile Asp Met Thr Thr Ile Leu Ser Leu Met Tyr Leu Ala Phe Val Ala
    210                 215                 220 aca att gtt ggt tat ggg atc tgg ggg acg tta ctg gga cgc tat gaa      720
Thr Ile Val Gly Tyr Gly Ile Trp Gly Thr Leu Leu Gly Arg Tyr Glu
225                 230                 235                 240 acc tgg cgg gtt gca ccg tta tcg tta ctg gtg ccc gta gta gga ctg      768
Thr Trp Arg Val Ala Pro Leu Ser Leu Leu Val Pro Val Val Gly Leu
                245                 250                 255 gca agt gcg gca cta ttg ttg gat gaa cgc tta acg ggt ctg caa ttt      816
Ala Ser Ala Ala Leu Leu Leu Asp Glu Arg Leu Thr Gly Leu Gln Phe
            260                 265                 270 tta ggt gcg gtg ctc att atg acc ggg ctg tat atc aat gta ttt ggc      864
Leu Gly Ala Val Leu Ile Met Thr Gly Leu Tyr Ile Asn Val Phe Gly
        275                 280                 285 ttg cgg tgg cgt aaa gcg gta aag gtg gga agt taa                      900
Leu Arg Trp Arg Lys Ala Val Lys Val Gly Ser
    290                 295
```

<210> SEQ ID NO 8
<211> LENGTH: 299
<212> TYPE: PRT
<213> ORGANISM: Escherichia coli

<400> SEQUENCE: 8

```
Met Ser Arg Lys Asp Gly Val Leu Ala Leu Val Val Val Val Trp
1               5                   10                  15

Gly Leu Asn Phe Val Val Ile Lys Val Gly Leu His Asn Met Pro Pro
            20                  25                  30

Leu Met Leu Ala Gly Leu Arg Phe Met Leu Val Ala Phe Pro Ala Ile
        35                  40                  45

Phe Phe Val Ala Arg Pro Lys Val Pro Leu Asn Leu Leu Gly Tyr
    50                  55                  60

Gly Leu Thr Ile Ser Phe Ala Gln Phe Ala Phe Leu Phe Cys Ala Ile
65                  70                  75                  80

Asn Phe Gly Met Pro Ala Gly Leu Ala Ser Leu Val Leu Gln Ala Gln
                85                  90                  95

Ala Phe Phe Thr Ile Met Leu Gly Ala Phe Thr Phe Gly Glu Arg Leu
            100                 105                 110

His Gly Lys Gln Leu Ala Gly Ile Ala Leu Ala Ile Phe Gly Val Leu
        115                 120                 125

Val Leu Ile Glu Asp Ser Leu Asn Gly Gln His Val Ala Met Leu Gly
    130                 135                 140

Phe Met Leu Thr Leu Ala Ala Ala Phe Ser Trp Ala Cys Gly Asn Ile
145                 150                 155                 160

Phe Asn Lys Lys Ile Met Ser His Ser Thr Arg Pro Ala Val Met Ser
                165                 170                 175

Leu Val Ile Trp Ser Ala Leu Ile Pro Ile Ile Pro Phe Phe Val Ala
            180                 185                 190

Ser Leu Ile Leu Asp Gly Ser Ala Thr Met Ile His Ser Leu Val Thr
        195                 200                 205

Ile Asp Met Thr Thr Ile Leu Ser Leu Met Tyr Leu Ala Phe Val Ala
    210                 215                 220

Thr Ile Val Gly Tyr Gly Ile Trp Gly Thr Leu Leu Gly Arg Tyr Glu
225                 230                 235                 240

Thr Trp Arg Val Ala Pro Leu Ser Leu Leu Val Pro Val Val Gly Leu
                245                 250                 255
```

```
Ala Ser Ala Ala Leu Leu Leu Asp Glu Arg Leu Thr Gly Leu Gln Phe
        260                 265                 270

Leu Gly Ala Val Leu Ile Met Thr Gly Leu Tyr Ile Asn Val Phe Gly
    275                 280                 285

Leu Arg Trp Arg Lys Ala Val Lys Val Gly Ser
    290                 295

<210> SEQ ID NO 9
<211> LENGTH: 40
<212> TYPE: DNA
<213> ORGANISM: Artificial Sequence
<220> FEATURE:
<223> OTHER INFORMATION: Synthetic DNA

<400> SEQUENCE: 9
acacaagctt atgcagaagt atatcagtga agcgcgtctg                        40

<210> SEQ ID NO 10
<211> LENGTH: 39
<212> TYPE: DNA
<213> ORGANISM: Artificial Sequence
<220> FEATURE:
<223> OTHER INFORMATION: Synthetic DNA

<400> SEQUENCE: 10
ttctggatcc ttagcgggat gctcgttgca gaatgatgg                         39

<210> SEQ ID NO 11
<211> LENGTH: 37
<212> TYPE: DNA
<213> ORGANISM: Artificial Sequence
<220> FEATURE:
<223> OTHER INFORMATION: Synthetic DNA

<400> SEQUENCE: 11
aaggaagctt atgaaaaggc aaagaaacgt caatttg                           37

<210> SEQ ID NO 12
<211> LENGTH: 38
<212> TYPE: DNA
<213> ORGANISM: Artificial Sequence
<220> FEATURE:
<223> OTHER INFORMATION: Synthetic DNA

<400> SEQUENCE: 12
aaaagagctc ttaaacgggc tgccctgat gcgacatc                           38

<210> SEQ ID NO 13
<211> LENGTH: 44
<212> TYPE: DNA
<213> ORGANISM: Artificial Sequence
<220> FEATURE:
<223> OTHER INFORMATION: Synthetic DNA

<400> SEQUENCE: 13
agagaagctt atggatgcaa acaaacgcg gcagggcgta ttac                    44

<210> SEQ ID NO 14
<211> LENGTH: 43
<212> TYPE: DNA
<213> ORGANISM: Artificial Sequence
<220> FEATURE:
<223> OTHER INFORMATION: Synthetic DNA

<400> SEQUENCE: 14
```

-continued aggggatcc ttatttggac gttctacgct gcgtataaat cgc     43

<210> SEQ ID NO 15
<211> LENGTH: 41
<212> TYPE: DNA
<213> ORGANISM: Artificial Sequence
<220> FEATURE:
<223> OTHER INFORMATION: Synthetic DNA

<400> SEQUENCE: 15
aagaaagctt atgtcgcgaa aagatggggt gttggcgcta c     41

<210> SEQ ID NO 16
<211> LENGTH: 41
<212> TYPE: DNA
<213> ORGANISM: Artificial Sequence
<220> FEATURE:
<223> OTHER INFORMATION: Synthetic DNA

<400> SEQUENCE: 16
aggaggatcc ttaacttccc acctttaccg ctttacgcca c     41

<210> SEQ ID NO 17
<211> LENGTH: 410
<212> TYPE: PRT
<213> ORGANISM: Escherichia coli

<400> SEQUENCE: 17

```
Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
            100                 105                 110

Ala Glu Leu Val Ile Gly Glu Leu Leu Leu Leu Arg Gly Val Pro
        115                 120                 125

Glu Ala Asn Ala Lys Ala His Arg Gly Val Trp Asn Lys Leu Ala Ala
    130                 135                 140

Gly Ser Phe Glu Ala Arg Gly Lys Lys Leu Gly Ile Ile Gly Tyr Gly
145                 150                 155                 160

His Ile Gly Thr Gln Leu Gly Ile Leu Ala Glu Ser Leu Gly Met Tyr
                165                 170                 175

Val Tyr Phe Tyr Asp Ile Glu Asn Lys Leu Pro Leu Gly Asn Ala Thr
            180                 185                 190

Gln Val Gln His Leu Ser Asp Leu Leu Asn Met Ser Asp Val Val Ser
        195                 200                 205

Leu His Val Pro Glu Asn Pro Ser Thr Lys Asn Met Met Gly Ala Lys
    210                 215                 220

Glu Ile Ser Leu Met Lys Pro Gly Ser Leu Leu Ile Asn Ala Ser Arg
225                 230                 235                 240

Gly Thr Val Val Asp Ile Pro Ala Leu Cys Asp Ala Leu Ala Ser Lys
```

```
                  245                 250                 255
His Leu Ala Gly Ala Ala Ile Asp Val Phe Pro Thr Glu Pro Ala Thr
                260                 265                 270

Asn Ser Asp Pro Phe Thr Ser Pro Leu Cys Glu Phe Asp Asn Val Leu
            275                 280                 285

Leu Thr Pro His Ile Gly Ser Thr Gln Glu Ala Gln Glu Asn Ile
        290                 295                 300

Gly Leu Glu Val Ala Gly Lys Leu Ile Lys Tyr Ser Asp Asn Gly Ser
305                 310                 315                 320

Thr Leu Ser Ala Val Asn Phe Pro Glu Val Ser Leu Pro Leu His Gly
                325                 330                 335

Gly Arg Arg Leu Met His Ile His Glu Asn Arg Pro Gly Val Leu Thr
            340                 345                 350

Ala Leu Asn Lys Ile Phe Ala Glu Gln Gly Val Asn Ile Ala Ala Gln
        355                 360                 365

Tyr Leu Gln Thr Ser Ala Gln Met Gly Tyr Val Ile Asp Ile Glu
        370                 375                 380

Ala Asp Glu Asp Val Ala Glu Lys Ala Leu Gln Ala Met Lys Ala Ile
385                 390                 395                 400

Pro Gly Thr Ile Arg Ala Arg Leu Leu Tyr
                405                 410

<210> SEQ ID NO 18
<211> LENGTH: 40
<212> TYPE: DNA
<213> ORGANISM: Artificial Sequence
<220> FEATURE:
<223> OTHER INFORMATION: Synthetic DNA

<400> SEQUENCE: 18
aaggaagctt atggcaaagg tatcgctgga gaaagacaag                      40

<210> SEQ ID NO 19
<211> LENGTH: 40
<212> TYPE: DNA
<213> ORGANISM: Artificial Sequence
<220> FEATURE:
<223> OTHER INFORMATION: Synthetic DNA

<400> SEQUENCE: 19
aaccagatct ttagtacagc agacgggcgc gaatggtacc                      40

<210> SEQ ID NO 20
<211> LENGTH: 17
<212> TYPE: DNA
<213> ORGANISM: Artificial Sequence
<220> FEATURE:
<223> OTHER INFORMATION: Synthetic DNA

<400> SEQUENCE: 20
tgggttcgac tcaggaa                                               17

<210> SEQ ID NO 21
<211> LENGTH: 16
<212> TYPE: DNA
<213> ORGANISM: Artificial Sequence
<220> FEATURE:
<223> OTHER INFORMATION: Synyhetic DNA

<400> SEQUENCE: 21
caatgtgtgg cgtcag                                                16
```

<210> SEQ ID NO 22
<211> LENGTH: 17
<212> TYPE: DNA
<213> ORGANISM: Artificial Sequence
<220> FEATURE:
<223> OTHER INFORMATION: Synthetic DNA

<400> SEQUENCE: 22
cgatcgccgc gcaatat                                              17

<210> SEQ ID NO 23
<211> LENGTH: 16
<212> TYPE: DNA
<213> ORGANISM: Artificial Sequence
<220> FEATURE:
<223> OTHER INFORMATION: Synthetic DNA

<400> SEQUENCE: 23
cgacgccctg ctcggc                                               16

<210> SEQ ID NO 24
<211> LENGTH: 27
<212> TYPE: DNA
<213> ORGANISM: Artificial Sequence
<220> FEATURE:
<223> OTHER INFORMATION: Synthetic DNA

<400> SEQUENCE: 24
cccgatctgc cgtatcgcgc cagtgaa                                   27

<210> SEQ ID NO 25
<211> LENGTH: 56
<212> TYPE: DNA
<213> ORGANISM: Artificial Sequence
<220> FEATURE:
<223> OTHER INFORMATION: Synthetic DNA

<400> SEQUENCE: 25
gaagcagctc cagcctacac gataatactc ctgacaaggt gactggactt ccagta   56

<210> SEQ ID NO 26
<211> LENGTH: 56
<212> TYPE: DNA
<213> ORGANISM: Artificial Sequence
<220> FEATURE:
<223> OTHER INFORMATION: Synthetic DNA

<400> SEQUENCE: 26
ctaaggagga tattcatatg tacttcttac tcgcccatct gcaacggatg ggcgaa   56

<210> SEQ ID NO 27
<211> LENGTH: 27
<212> TYPE: DNA
<213> ORGANISM: Artificial Sequence
<220> FEATURE:
<223> OTHER INFORMATION: Synthetic DNA

<400> SEQUENCE: 27
gccgcctgtt tacgtaatgg caaatgg                                   27

<210> SEQ ID NO 28
<211> LENGTH: 30
<212> TYPE: DNA
<213> ORGANISM: Artificial Sequence
<220> FEATURE:
<223> OTHER INFORMATION: Synthetic DNA -continued

<400> SEQUENCE: 28
gtgaaaacgc gcgccgccat taccgcatca                              30

<210> SEQ ID NO 29
<211> LENGTH: 56
<212> TYPE: DNA
<213> ORGANISM: Artificial Sequence
<220> FEATURE:
<223> OTHER INFORMATION: Synthetic DNA

<400> SEQUENCE: 29
gaagcagctc cagcctacac gagcggagat tacgtgcaga tttcgtagca agggat    56

<210> SEQ ID NO 30
<211> LENGTH: 56
<212> TYPE: DNA
<213> ORGANISM: Artificial Sequence
<220> FEATURE:
<223> OTHER INFORMATION: Synthetic DNA

<400> SEQUENCE: 30
ctaaggagga tattcatatg tagcctgttc cggcatcgaa tgttacccct atcgcc      56

<210> SEQ ID NO 31
<211> LENGTH: 30
<212> TYPE: DNA
<213> ORGANISM: Artificial Sequence
<220> FEATURE:
<223> OTHER INFORMATION: Synthetic DNA

<400> SEQUENCE: 31 gtagcccttta tctgtcgaaa caatcgttgc                              30

<210> SEQ ID NO 32
<211> LENGTH: 27
<212> TYPE: DNA
<213> ORGANISM: Artificial Sequence
<220> FEATURE:
<223> OTHER INFORMATION: Synthetic DNA

<400> SEQUENCE: 32
ggttaacttt ggccccgttt ccaccag                                  27

<210> SEQ ID NO 33
<211> LENGTH: 56
<212> TYPE: DNA
<213> ORGANISM: Artificial Sequence
<220> FEATURE:
<223> OTHER INFORMATION: Synthetic DNA

<400> SEQUENCE: 33
gaagcagctc cagcctacac ggcggtcctg ttggacaacg gcgaacagta taccg     56

<210> SEQ ID NO 34
<211> LENGTH: 56
<212> TYPE: DNA
<213> ORGANISM: Artificial Sequence
<220> FEATURE:
<223> OTHER INFORMATION: Synthetic DNA

<400> SEQUENCE: 34
ctaaggagga tattcatatg cggtgatttg ctgtcaatgt gctcgttgtt catgcc    56

<210> SEQ ID NO 35
<211> LENGTH: 27
<212> TYPE: DNA

<213> ORGANISM: Artificial Sequence
<220> FEATURE:
<223> OTHER INFORMATION: Synthetic DNA

<400> SEQUENCE: 35
tcagatttgg ttgtacggtc gcagttg                                27

<210> SEQ ID NO 36
<211> LENGTH: 33
<212> TYPE: DNA
<213> ORGANISM: Artificial Sequence
<220> FEATURE:
<223> OTHER INFORMATION: Synthetic DNA

<400> SEQUENCE: 36
tatatcgatc aaaaaggcaa cactatgaca tcg                         33

<210> SEQ ID NO 37
<211> LENGTH: 33
<212> TYPE: DNA
<213> ORGANISM: Artificial Sequence
<220> FEATURE:
<223> OTHER INFORMATION: Synthetic DNA

<400> SEQUENCE: 37
ttaggatcct catcaggttg gatcaacagg cac                         33

<210> SEQ ID NO 38
<211> LENGTH: 30
<212> TYPE: DNA
<213> ORGANISM: Artificial Sequence
<220> FEATURE:
<223> OTHER INFORMATION: Synthetic DNA

<400> SEQUENCE: 38
actagatcta acaggatcgc catcatgcaa                             30

<210> SEQ ID NO 39
<211> LENGTH: 33
<212> TYPE: DNA
<213> ORGANISM: Artificial Sequence
<220> FEATURE:
<223> OTHER INFORMATION: Synthetic DNA

<400> SEQUENCE: 39
ataggatcct taagccacgc gagccgtcag ctg                         33

<210> SEQ ID NO 40
<211> LENGTH: 27
<212> TYPE: DNA
<213> ORGANISM: Artificial Sequence
<220> FEATURE:
<223> OTHER INFORMATION: Synthetic DNA

<400> SEQUENCE: 40
gcgatctggt gcttacctgt accgaca                                27

<210> SEQ ID NO 41
<211> LENGTH: 56
<212> TYPE: DNA
<213> ORGANISM: Artificial Sequence
<220> FEATURE:
<223> OTHER INFORMATION: Synthetic DNA

<400> SEQUENCE: 41
gaagcagctc cagcctacac tgcttactcc acacgatgag ataatgaccg gcccgt    56

```
<210> SEQ ID NO 42
<211> LENGTH: 56
<212> TYPE: DNA
<213> ORGANISM: Artificial Sequence
<220> FEATURE:
<223> OTHER INFORMATION: Synthetic DNA

<400> SEQUENCE: 42
ctaaggagga tattcatatg tgtcctgtga tcgtgccgga tgcgatgtaa tcatct        56

<210> SEQ ID NO 43
<211> LENGTH: 27
<212> TYPE: DNA
<213> ORGANISM: Artificial Sequence
<220> FEATURE:
<223> OTHER INFORMATION: Synthetic DNA

<400> SEQUENCE: 43
ccgttacgcg tcatcatgac tatcgcg                                         27

<210> SEQ ID NO 44
<211> LENGTH: 33
<212> TYPE: DNA
<213> ORGANISM: Artificial Sequence
<220> FEATURE:
<223> OTHER INFORMATION: Synthetic DNA

<400> SEQUENCE: 44
atgctggtct atatccattg atggcttatc gct                                  33

<210> SEQ ID NO 45
<211> LENGTH: 33
<212> TYPE: DNA
<213> ORGANISM: Artificial Sequence
<220> FEATURE:
<223> OTHER INFORMATION: Synthetic DNA

<400> SEQUENCE: 45
ccatcaatgg atatagacca gcatttcaac ggt                                  33

<210> SEQ ID NO 46
<211> LENGTH: 40
<212> TYPE: DNA
<213> ORGANISM: Artificial Sequence
<220> FEATURE:
<223> OTHER INFORMATION: Synthetic DNA

<400> SEQUENCE: 46
ggggaagctt atgtcgtgtg aagaactgga aattgtctgg                           40

<210> SEQ ID NO 47
<211> LENGTH: 41
<212> TYPE: DNA
<213> ORGANISM: Artificial Sequence
<220> FEATURE:
<223> OTHER INFORMATION: Synthetic DNA

<400> SEQUENCE: 47 gggggggatcc ttagatccca tccccatact caaatgtatg g                        41
```